United States Patent
Wodlinger et al.

(10) Patent No.: US 11,051,790 B2
(45) Date of Patent: Jul. 6, 2021

(54) SYSTEM COMPRISING INDICATOR FEATURES IN HIGH-RESOLUTION MICRO-ULTRASOUND IMAGES

(71) Applicant: EXACT IMAGING, INC., Ontario (CA)

(72) Inventors: Brian Wodlinger, Ontario (CA); Theresa McGrath, Ontario (CA); Jerrold Wen, Ontario (CA)

(73) Assignee: Exact Imaging, Inc., Markham (CA)

( * ) Notice: Subject to any disclaimer, the term of this patent is extended or adjusted under 35 U.S.C. 154(b) by 399 days.

(21) Appl. No.: 15/775,216

(22) PCT Filed: Nov. 10, 2016

(86) PCT No.: PCT/CA2016/051313
§ 371 (c)(1),
(2) Date: May 10, 2018

(87) PCT Pub. No.: WO2017/079843
PCT Pub. Date: May 18, 2017

(65) Prior Publication Data
US 2018/0333140 A1 Nov. 22, 2018

Related U.S. Application Data

(60) Provisional application No. 62/253,310, filed on Nov. 10, 2015.

(51) Int. Cl.
*A61B 8/08* (2006.01)
*A61B 8/12* (2006.01)
(Continued)

(52) U.S. Cl.
CPC ............ *A61B 8/5223* (2013.01); *A61B 8/085* (2013.01); *A61B 8/12* (2013.01); *A61B 8/481* (2013.01);
(Continued)

(58) Field of Classification Search
CPC ......... A61B 8/08; A61B 8/5246; A61B 8/483; A61B 8/481; A61B 8/12; A61B 8/485;
(Continued)

(56) References Cited

U.S. PATENT DOCUMENTS 6,385,474 B1 * 5/2002 Rather .................... A61B 8/08
128/920
7,556,602 B2 * 7/2009 Wang .................... A61B 6/463
600/437

(Continued)

FOREIGN PATENT DOCUMENTS

WO   2014/186899 A1   11/2014

OTHER PUBLICATIONS

International Search Report, PCT/CA2016/051313, dated Feb. 6, 2017.

*Primary Examiner* — Oommen Jacob
(74) *Attorney, Agent, or Firm* — Baker & Hostetler LLP

(57) ABSTRACT

This invention provides a system and method for providing Indicator Features in high resolution micro-ultrasound prostate images, wherein the ultrasound device operates at a center frequency of 15 MHz and above. Indicator Features are features, which have been identified alone and/or in combination with other features in high resolution micro-ultrasound images, and have been determined to be significantly statistically correlated to either benign tissue or some grade of cancerous tissue on the basis of predictive probabilities. These Indicator Features can be used to train a linear or non-linear classifier, which can be used to classify patient images of the prostate. These Indicator Features can be used to guide a clinician as to where to take a biopsy core from the prostate, as well as assist in diagnosis of the tissue.

11 Claims, 18 Drawing Sheets

(51) Int. Cl.
| | |
|---|---|
| *G06T 7/00* | (2017.01) |
| *G16H 50/20* | (2018.01) |
| *G16H 30/40* | (2018.01) |
| *G16H 40/63* | (2018.01) |
| *G06T 7/11* | (2017.01) |
| *G06K 9/46* | (2006.01) |
| *G06K 9/62* | (2006.01) |
| *G06F 16/00* | (2019.01) |

(52) U.S. Cl.
CPC .............. *A61B 8/483* (2013.01); *A61B 8/485* (2013.01); *A61B 8/488* (2013.01); *A61B 8/5246* (2013.01); *G06K 9/46* (2013.01); *G06K 9/628* (2013.01); *G06K 9/6257* (2013.01); *G06K 9/6277* (2013.01); *G06T 7/0012* (2013.01); *G06T 7/0014* (2013.01); *G06T 7/11* (2017.01); *G16H 30/40* (2018.01); *G16H 40/63* (2018.01); *G16H 50/20* (2018.01); *G06F 16/00* (2019.01); *G06K 2209/051* (2013.01); *G06T 2207/10132* (2013.01); *G06T 2207/20076* (2013.01); *G06T 2207/20081* (2013.01); *G06T 2207/20084* (2013.01); *G06T 2207/30081* (2013.01); *G06T 2207/30096* (2013.01)

(58) Field of Classification Search
CPC ....... A61B 8/488; A61B 8/5223; A61B 8/085; G16H 30/40; G16H 50/20; G16H 40/63; G06T 7/11; G06T 7/0012; G06T 7/0014; G06T 2207/30081; G06T 2207/20081; G06T 2207/10132; G06T 2207/20084; G06T 2207/30096; G06T 2207/20076; G06T 7/143; G06T 2207/30028; G06T 2207/30061; G06K 9/628; G06K 9/6257; G06K 9/6277; G06K 9/46; G06K 2209/051; G06K 9/00; G06K 9/6278; G06K 2209/053; G06K 2209/05; G06F 16/00

See application file for complete search history.

(56) References Cited

U.S. PATENT DOCUMENTS

| | | | |
|---|---|---|---|
| 7,876,943 B2 | 1/2011 | Jerebko et al. | |
| 8,440,409 B2* | 5/2013 | Zhang | A61P 35/00 435/7.1 |
| 8,488,863 B2* | 7/2013 | Boucheron | G06T 7/11 382/133 |
| 2002/0065466 A1* | 5/2002 | Rather | A61B 8/08 600/447 |
| 2003/0007598 A1* | 1/2003 | Wang | A61B 8/5238 378/37 |
| 2007/0055126 A1* | 3/2007 | Yu | A61B 5/4381 600/407 |
| 2008/0039723 A1 | 2/2008 | Suri et al. | |
| 2008/0170770 A1 | 7/2008 | Suri et al. | |
| 2009/0046905 A1* | 2/2009 | Lange | G06T 7/30 382/128 |
| 2009/0088640 A1* | 4/2009 | Park | G06K 9/6257 600/453 |
| 2010/0003238 A1* | 1/2010 | Frost | A61P 35/04 424/94.62 |
| 2010/0111396 A1* | 5/2010 | Boucheron | G06K 9/6231 382/133 |
| 2010/0329529 A1* | 12/2010 | Feldman | G06K 9/4619 382/131 |
| 2012/0040861 A1* | 2/2012 | Williams | G01N 33/6893 506/9 |
| 2012/0136255 A1 | 5/2012 | Fan et al. | |
| 2012/0163693 A1* | 6/2012 | Suri | G06T 7/0012 382/131 |
| 2013/0123630 A1 | 5/2013 | Freiburger et al. | |
| 2014/0314292 A1* | 10/2014 | Kamen | G16H 20/40 382/131 |
| 2015/0030255 A1* | 1/2015 | Wu | G06K 9/00664 382/224 |
| 2015/0118221 A1* | 4/2015 | Chatterjee | G01N 33/573 424/130.1 |
| 2016/0238568 A1* | 8/2016 | Feleppa | G01N 29/4472 |
| 2018/0333140 A1* | 11/2018 | Wodlinger | A61B 8/5246 |

* cited by examiner

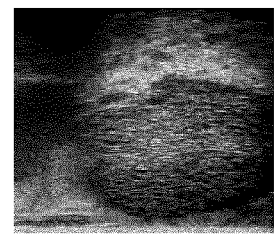
Figure 11A
Figure 11B
Figure 11C
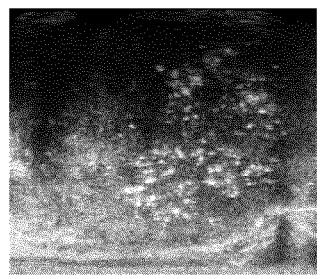
Figure 11D
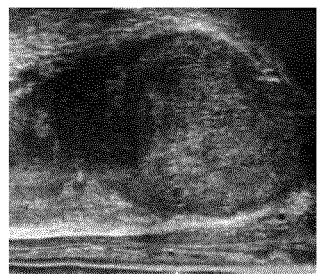
Figure 11E
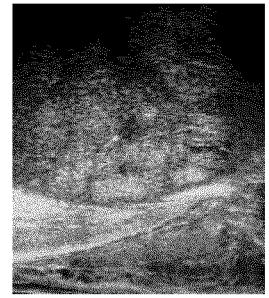
Figure 11F
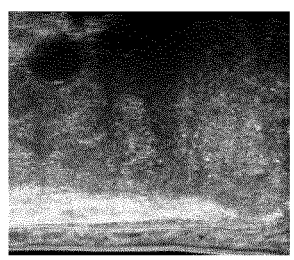
Figure 11G
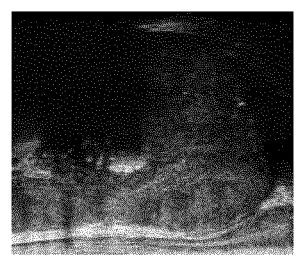
Figure 11H
FIG. 11

| Feature | Avg Risk Score | N(Cancer)/N | Use for Training? |
|---|---|---|---|
| Heterogenous-Bright Echos-Finger/Funky Shadows | 5 | 1/1 | Good Cancer Predictor |
| Heterogenous-Finger/Funky Shadows | 5 | 3/3 | Good Cancer Predictor |
| Heterogenous-Coarse-Shadows | 4.5 | 2/2 | Good Cancer Predictor |
| Heterogenous-Hyperechoic-Coarse | 4.5 | 1/2 | Unclear/Chance Level |
| Heterogenous-Irregular | 4.5 | 4/6 | Good Cancer Predictor |
| Heterogenous-Lesion | 4.5 | 2/2 | Good Cancer Predictor |
| Heterogenous-Coarse-Finger/Funky Shadows | 4.3 | 3/3 | Good Cancer Predictor |
| Heterogenous-Irregular-Coarse | 4.3 | 1/2 | Unclear/Chance Level |
| Heterogenous-Shadows | 4.2 | 2/3 | Good Cancer Predictor |
| Heterogenous-Defined | 4 | 1/3 | Good Benign Predictor |
| Heterogenous-Defined-Coarse | 4 | 1/1 | Not Enough Data |
| Heterogenous-Hyperechoic | 4 | 0/2 | Good Benign Predictor |
| Heterogenous-Hyperechoic-Irregular | 4 | 1/1 | Not Enough Data |
| Heterogenous-Hypoechoic-Lesion-Bright Echos | 4 | 1/1 | Not Enough Data |
| Hyperechoic-Coarse-Shadows | 4 | 0/1 | Not Enough Data |
| Hyperechoic-Hypoechoic-Defined | 4 | 1/1 | Not Enough Data |
| Hyperechoic-Hypoechoic-Lesion-Bright Echos | 4 | 0/1 | Not Enough Data |
| Hypoechoic | 4 | 0/1 | Not Enough Data |
| Hypoechoic-Bright Echos-Coarse | 4 | 0/1 | Not Enough Data |
| Heterogenous-Bright Echos-Coarse | 3.9 | 11/14 | Good Cancer Predictor |
| Heterogenous-Bright Echos | 3.5 | 7/16 | Unclear/Chance Level |
| Heterogenous-Coarse | 3.5 | 15/22 | Good Cancer Predictor |
| Hyperechoic-Hypoechoic-Lesion-Coarse | 3.5 | 1/2 | Unclear/Chance Level |
| Hypoechoic-Defined | 3.5 | 1/1 | Not Enough Data |
| Hyperechoic-Bright Echos-Coarse | 3.1 | 4/8 | Unclear/Chance Level |
| Anechoic-Heterogenous-Defined | 3 | 0/1 | Not Enough Data |
| Heterogenous | 3 | 6/12 | Unclear/Chance Level |
| Heterogenous-Hypoechoic-Lesion-Coarse | 3 | 1/1 | Not Enough Data |
| Hyperechoic-Coarse-Irregular Prostate Borders | 3 | 0/1 | Not Enough Data |
| Hyperechoic-Coarse-Microgranulomas | 3 | 0/1 | Not Enough Data |
| Hyperechoic-Hypoechoic-Bright Echos | 3 | 1/1 | Not Enough Data |
| Hyperechoic-Hypoechoic-Lesion | 3 | 1/1 | Not Enough Data |
| Hypoechoic-Lesion-Bright Echos-Coarse | 3 | 0/1 | Not Enough Data |
| Hypoechoic-Undefined/Vague | 3 | 1/1 | Not Enough Data |
| Hyperechoic-Hypoechoic | 2.8 | 1/3 | Good Benign Predictor |
| Hyperechoic-Bright Echos | 2.6 | 2/5 | Unclear/Chance Level |
| Hyperechoic-Coarse | 2.4 | 8/26 | Good Benign Predictor |
| Anechoic-Hyperechoic-Defined | 2.3 | 1/3 | Good Benign Predictor |
| Hyperechoic | 2.3 | 2/13 | Good Benign Predictor |
| Bright Echos | 2 | 0/1 | Not Enough Data |
| Bright Echos-Coarse | 2 | 0/1 | Not Enough Data |
| Coarse | 2 | 0/1 | Not Enough Data |
| Heterogenous-Hyperechoic-Lesion | 2 | 0/1 | Not Enough Data |
| Coarse-Small Ducts | 1.7 | 0/3 | Good Benign Predictor |
| Small Ducts | 1 | 0/1 | Not Enough Data |

FIG. 15

SYSTEM COMPRISING INDICATOR FEATURES IN HIGH-RESOLUTION MICRO-ULTRASOUND IMAGES

CROSS-REFERENCE TO RELATED APPLICATIONS

This application is the National Stage of International Patent Application No. PCT/CA2016/051313, filed Nov. 10, 2016, which claims priority from U.S. Patent Application No. 62/253,310, filed Nov. 10, 2015, the disclosures of each of which are incorporated herein by reference in their entireties for any and all purposes.

FIELD OF THE INVENTION

The present disclosure relates generally to medical imaging and diagnostics, and more specifically to Indicator Features in high resolution micro-ultrasound images of the prostate.

SUMMARY

This invention provides a system and method for providing Indicator Features in high resolution micro-ultrasound prostate images, wherein the ultrasound device operates at a center frequency of 15 MHz and above. These Indicator Features can be used to train a linear or non-linear classifier, which can be used to classify patient images of the prostate. These Indicator Features can be used to guide a clinician as to where to take a biopsy core from the prostate, as well as assist in diagnosis of the tissue.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND TO THE INVENTION

The prostate is a walnut sized gland found beneath the bladder and in front of the rectum that surrounds part of the male urethra. The prostate goes through two main periods of growth. In early puberty, the prostate doubles in size, and then, around age 25, the prostate begins to grow again and continues to grow throughout most of a man's life. The continuing enlargement of the prostate does not usually cause problems until later in life. There are three main disorders of the prostate, which can be reflected in ultrasound images: Benign Prostatic Hyperplasia (BPH); Prostatitis; and Prostatic Cancer.

Benign prostatic hypertrophy or hyperplasia (BPH) is one of the most common medical problems experienced by men over 50 years old. Hyperplastic enlargement of the prostate gland, or enlargement due to abnormal but benign multiplication of the cells thereof, often leads to compression of the urethra thereby resulting in obstruction of the urinary tract. Benign prostatic hyperplasia is due to a combination of stromal and glandular hyperplasia, predominantly of the transitional zone (as opposed to prostate cancer, which typically originates in the peripheral zone).

Unlike BPH, which occurs primarily in older men, prostatitis can occur in both younger (men in age groups of 18-50) and older men (over the age of 50), with the median reported patient age at about 40 years of age. There are several classifications or types of prostatitis, each of which may have different characteristics, manifestations, symptoms, or treatment protocols. Type I is acute bacterial prostatitis; Type II is chronic bacterial prostatitis; Type III is chronic (non-bacterial) prostatitis and/or chronic pelvic pain syndrome (CPPS); and Type IV is asymptomatic inflammatory prostatitis.

Prostate cancer is the most prevalent newly diagnosed malignancy in men, second only to lung cancer in causing cancer-related deaths. Clinically localized disease is usually suspected based on an elevated prostate specific antigen (PSA) test or abnormal digital rectal exam (DRE), prompting transrectal ultrasound (TRUS) guided biopsy of the prostate for definitive diagnosis. TRUS however, is not reliable enough to be used solely as a template for biopsy. There are cancers that are not visible (isoechoic) on TRUS. Furthermore, in PSA screened populations, the accuracy of TRUS was only 52% due to false-positive findings encountered. Increased tumor vessels (angiogenesis) have been shown microscopically in prostate cancer compared with benign prostate tissue.

Efficacy of color and power Doppler ultrasound for targeting cancer has not been demonstrated, probably due to limited resolution and small flow velocities. Elasticity imaging, with its many variants, is a new modality that is currently under extensive investigation. It is evident that given the limitations of the present diagnostic protocols, development of a new imaging modality that improves visualization and biopsy yield of prostate cancer would be beneficial.

Appropriate imaging of prostate cancer is a crucial component for diagnosing prostate cancer and its staging, in addition to PSA levels and DRE. The current state of prostate imaging for diagnosis of prostate cancer includes ultrasound, ultrasound-guided prostate biopsies, magnetic resonance imaging (MRI), and nuclear scinitigraphy. These modalities are helpful, but have drawbacks and limitations. MRI is expensive and not mobile. Nuclear scintillation is expensive, provides low resolution planar images, and there are problems with radiotracer excretion through the kidneys. Both these modalities are not available for general use.

Ultrasound imaging is relatively quick and inexpensive, and is less invasive with fewer potential side effects than other types of imaging such as X-Ray and MRI. Transrectal ultrasound (TRUS) guided prostate biopsy is the current standard of care for the diagnosis of prostate cancer, and may be indicated in the setting of an elevated PSA, abnormal DRE, and/or abnormality of other serum or urinary tests specific for prostate cancer (e.g. PHI, PCA3).

However, conventional ultrasound technology has limitations that make it unsuitable for some applications. For example, ultrasound waves do not pass well through certain types of tissues and anatomical features, and ultrasound images typically have weaker contrast and lower spatial resolution than X-Ray and MRI images. Also, ultrasonic imaging has difficulties distinguishing between acoustically homogenous tissues (i.e. tissues having similar ultrasonic properties).

In essence, conventional ultrasound images only demonstrate the possibility of revealing dark spots (hypoechoic areas), which correlate very poorly with cancer. There are no identifiable patterns in the image that can be reliably correlated with cancerous tissue. In many cases prostate cancer appears as an isoechoic lesion (similar gray scale value as surrounding tissue) causing high miss rate. When it is visible (hyper or hypoechoic), it is not possible to say with certainty if it is cancer or benign because many other non-cancer conditions such as prostate atrophy, inflammation of the prostate gland, and benign tumors may also look similar in appearance on ultrasound examination. While hypoechoic areas are often (approximately 50% of cases) seen on conventional transrectal ultrasound (Däihnert W F et al: Radiology 1986, 158: 97; Toi A: The Prostate: In: Diagnostic Ultrasound $4^{th}$ Edition: Maryland Heights: Mosby 2011, pp 392-428; Carter H B et al: J. Urol. 1989, 142: 1008) their value in predicting biopsy malignancy is poor, providing a positive predictive value of only 18-42% (Loch T. et al: World J. Urol. 22: 357; Flanigan R C et al: J. Urol. 1994 152: 1506). More importantly, taking targeted biopsies of only these areas has a high false negative rate, missing clinically significant cancer in up to 48% of patients with proven disease on radical prostatectomy (Carter H B et al: J. Urol. 1989, 142: 1008).

A biopsy has to be performed on the suspect lesion for definitive diagnosis. Biopsies are uncomfortable and bleeding may result as a complication. Because of poor lesion detection, even the current prostate biopsy techniques miss approximately 30% of prostate cancer. Utility of color flow and power Doppler in conjunction with gray scale ultrasound has been explored, but has not achieved wide-spread use.

This has resulted in ultrasound being used primarily for biopsy guidance through visualizing the prostate borders and midline in order to appropriately space and extract 8-12 systematic biopsy samples. These samples are typically taken systematically with a bias toward the lateral portions of the prostate in order to preferentially sample the peripheral zone. While they provide some level of consistency and are very likely to find larger tumors, smaller cancers and atypically located cancers may be missed. Indeed cancer detection rates using conventional systematic TRUS-biopsy range between approximately 20-50%. (Sing H, et al: J. Urol. 2004, 171: 1088; Jones J S et al: J. Urol. 2006, 175: 485; Shariat S F et al: Rev. Urol. 2008, 10, 262; Siu W et al: J. Urol. 2005, 174: 505), meaning that some 60-80% of men undergo this procedure unnecessarily. These patients often undergo repeat or saturation biopsies, often in combination with more costly and specialized imaging such as MRI. These further procedures come with increased costs, complexity, and an increased risk of morbidity both due to the repeated procedures themselves and to potential delays in diagnosis which can lead to decreased opportunity for cure. Therefore, there is an urgent need for a new imaging methodology that will have widespread utility as a tool for primary screening and diagnosis of prostate cancer.

Advances in ultrasound technology have created new high frequency imaging systems. High frequency ultrasound refers to ultrasound systems which can transmit ultrasound at a center transducer frequency of 15 MHz or higher, compared to 6-9 MHz center on conventional clinical prostate ultrasound imaging systems. Exemplary micro-ultrasound devices (ExactVu™, Exact Imaging, Toronto, Canada) operate at 29 MHz (21 MHz center). This increased frequency provides superior spatial resolution down to 70 microns, leading to 300% improved resolution over existing platforms. These improvements in resolution provide as yet unseen detail in prostate ultrasound images, which may enable improved visualization and targeting of suspicious regions as well as systematic image-guided prostate biopsy.

Yet, a need remains for identifying what prostate cancer looks like in a high resolution ultrasound image of the prostate with a selected statistical confidence. Additionally there is a need for a system assisting in diagnosis of prostate cancer by reducing the rate of false negative by guiding biopsies to suspicious patches of tissue or to allow targeted biopsies of high risk tissues in the prostate.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

FIGURES

The foregoing and other features and advantages of the subject matter disclosed herein will be made apparent from the following detailed description taken in conjunction with the accompanying drawings, in which.

Figure 12:
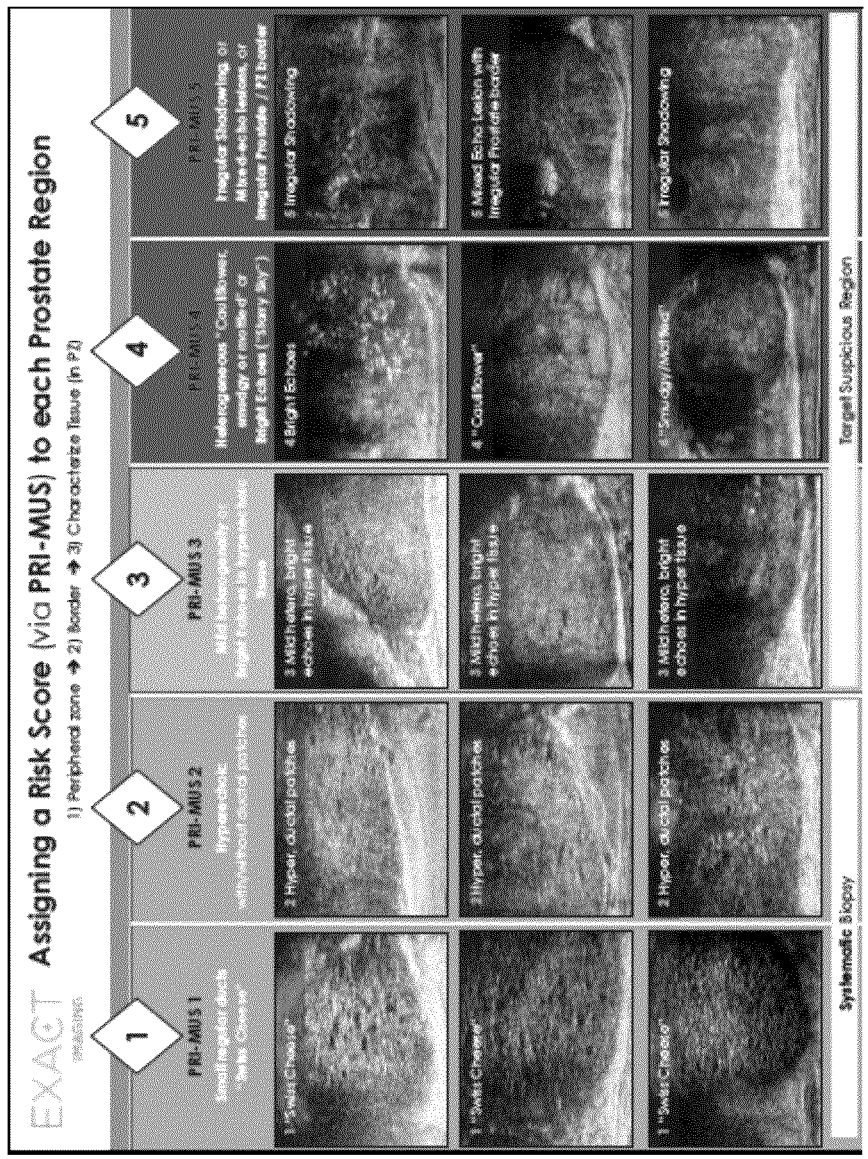
Figure 13:
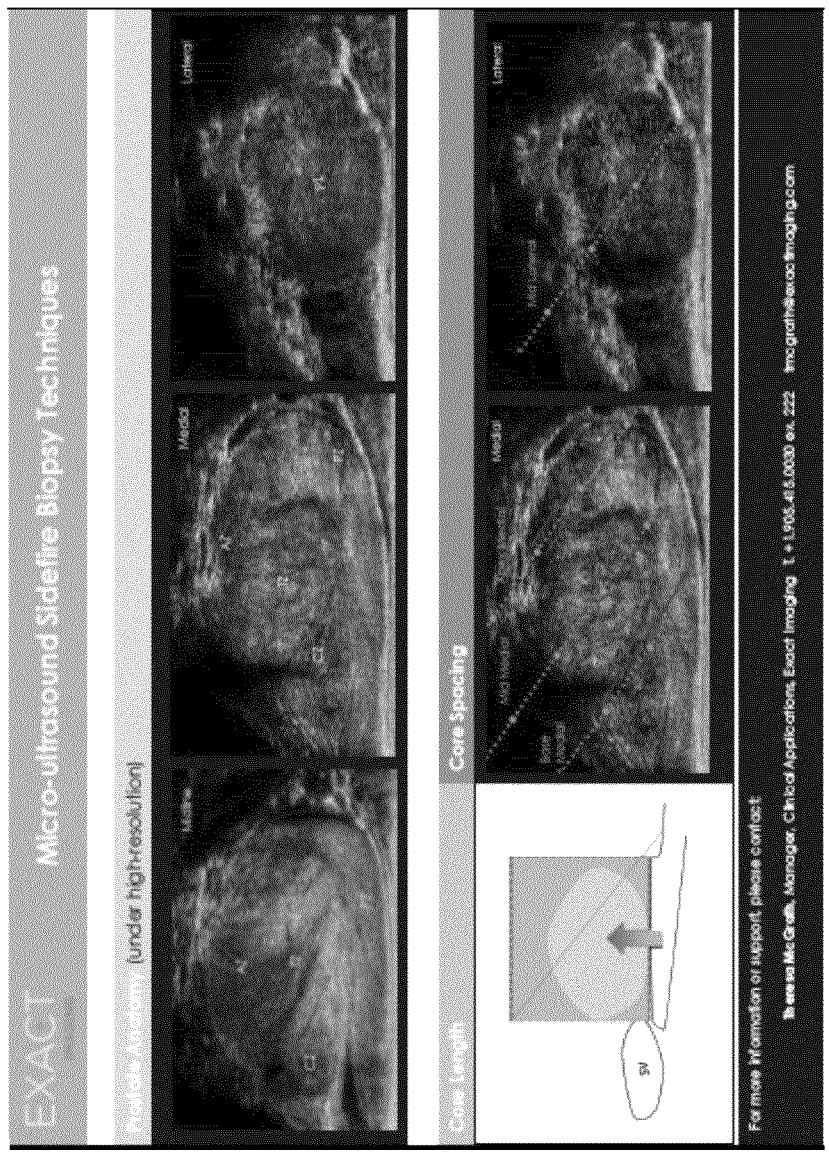
Figure 14:
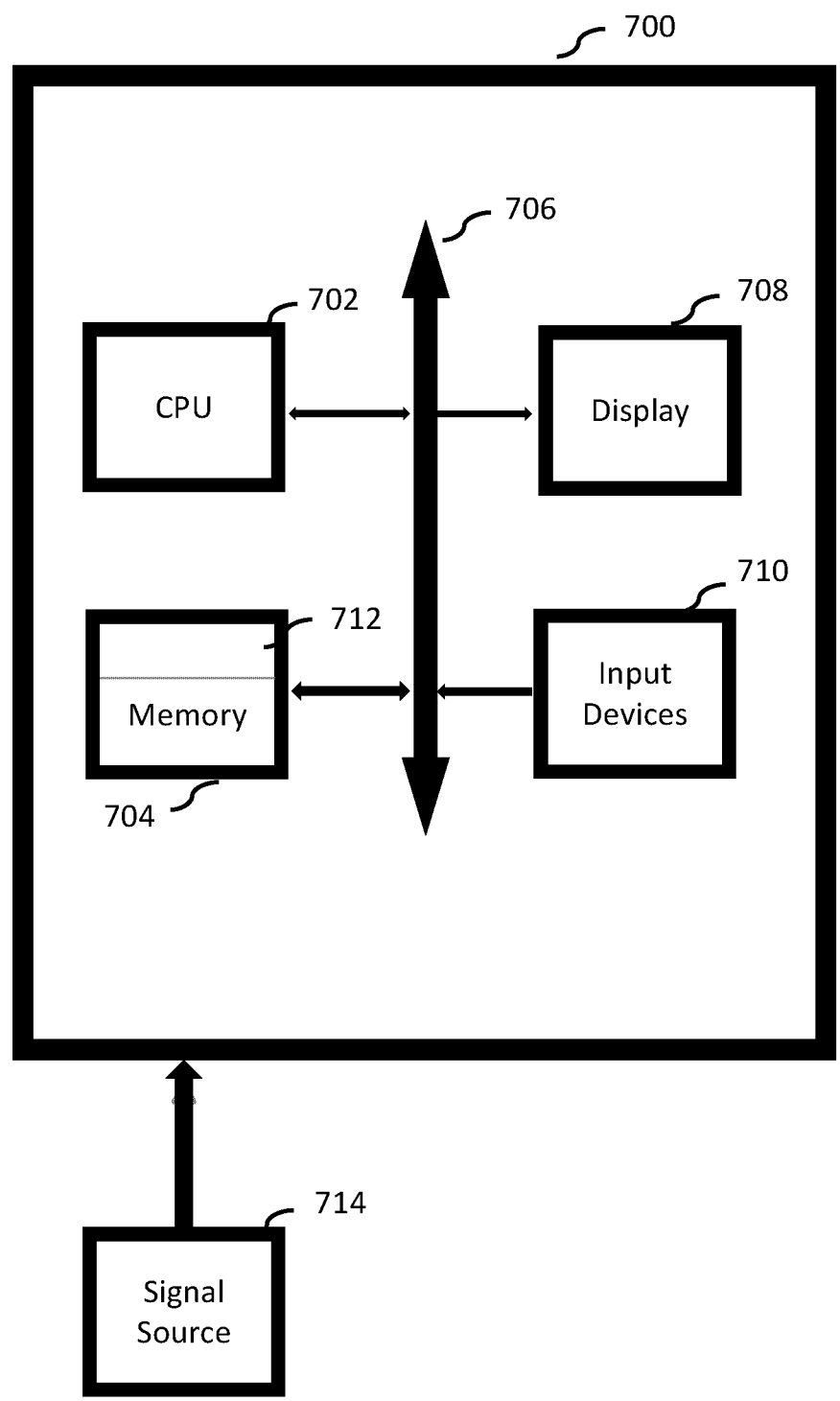
Figure 16:
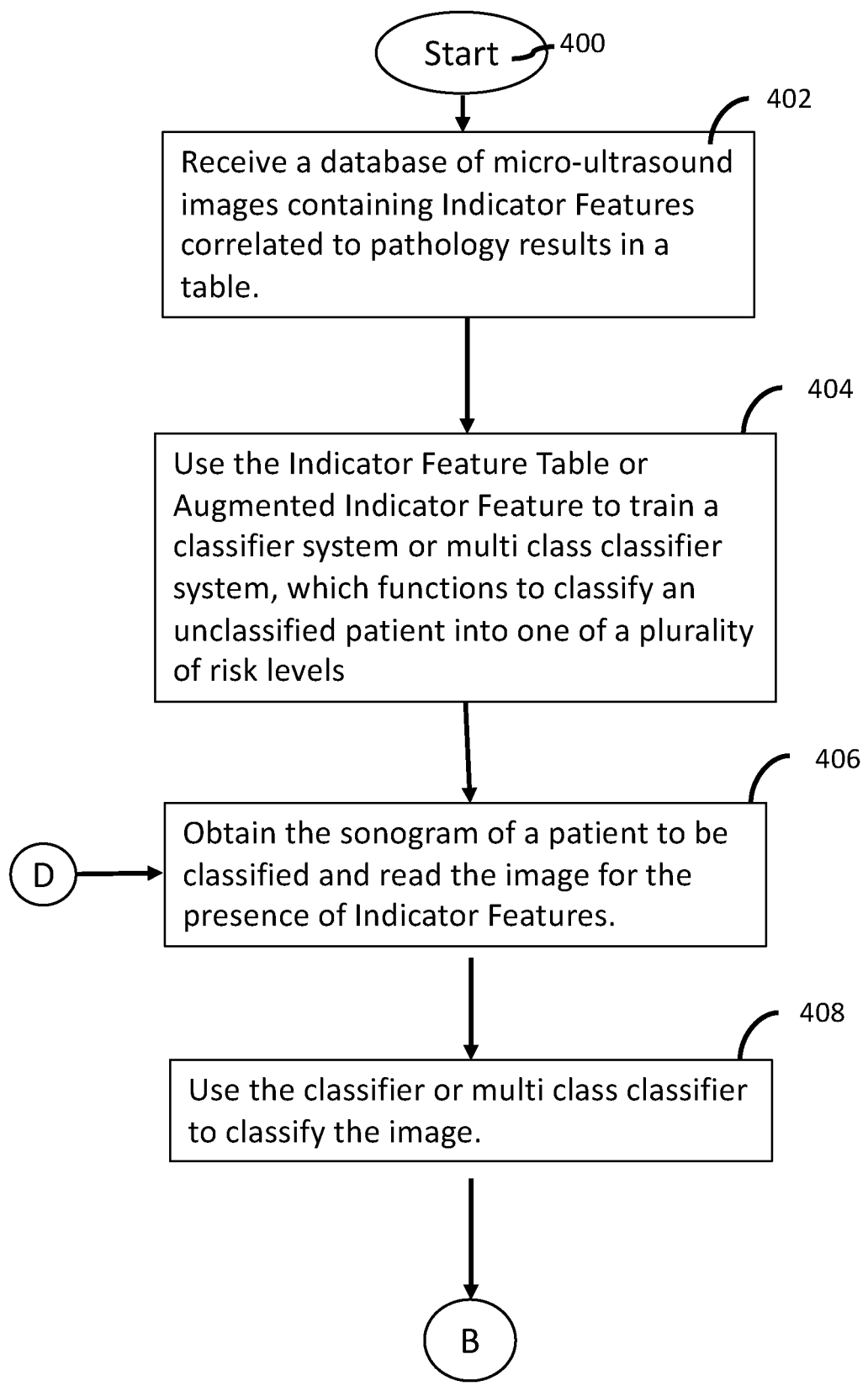
Figure 17:
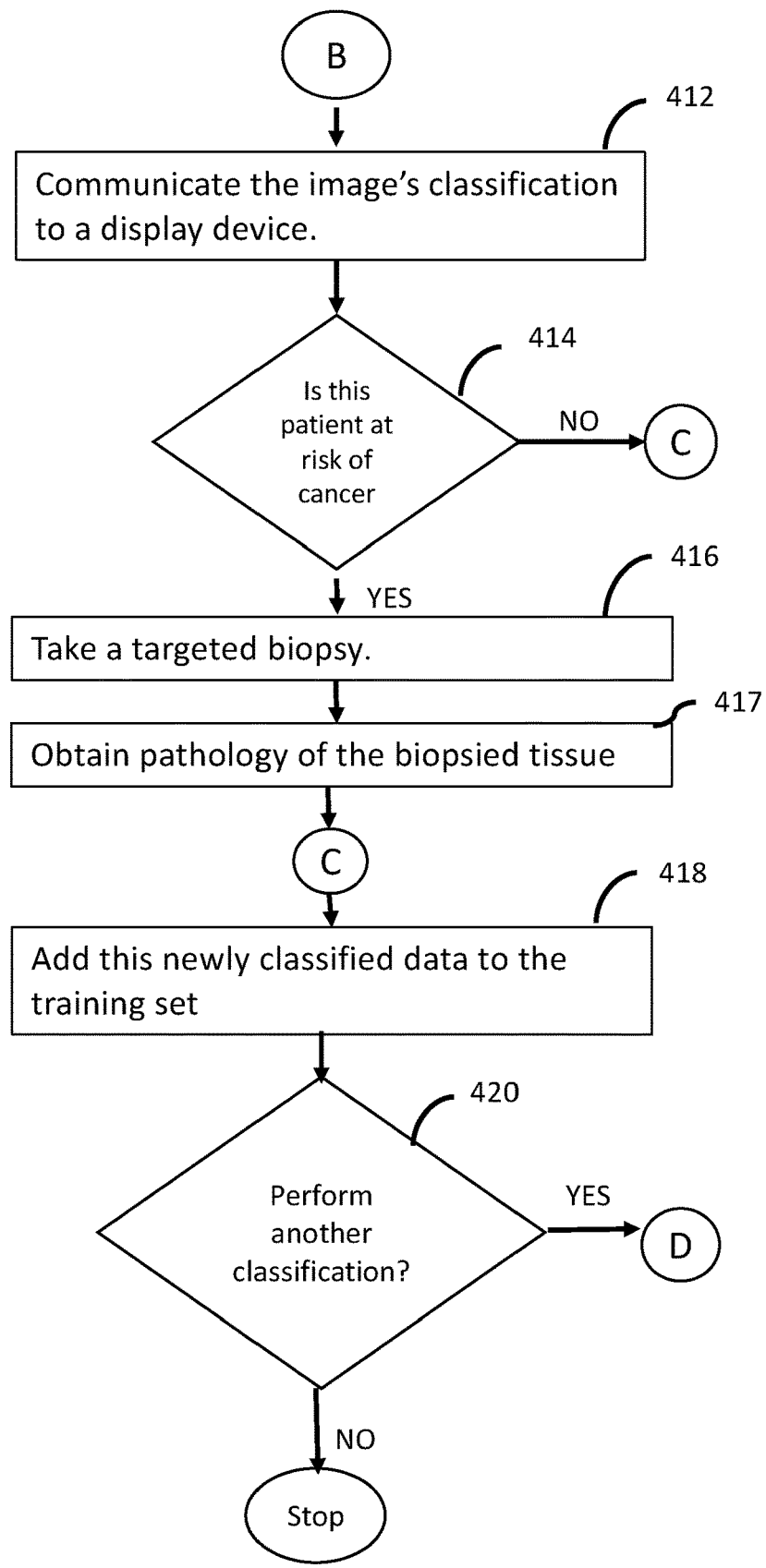
Figure 18:
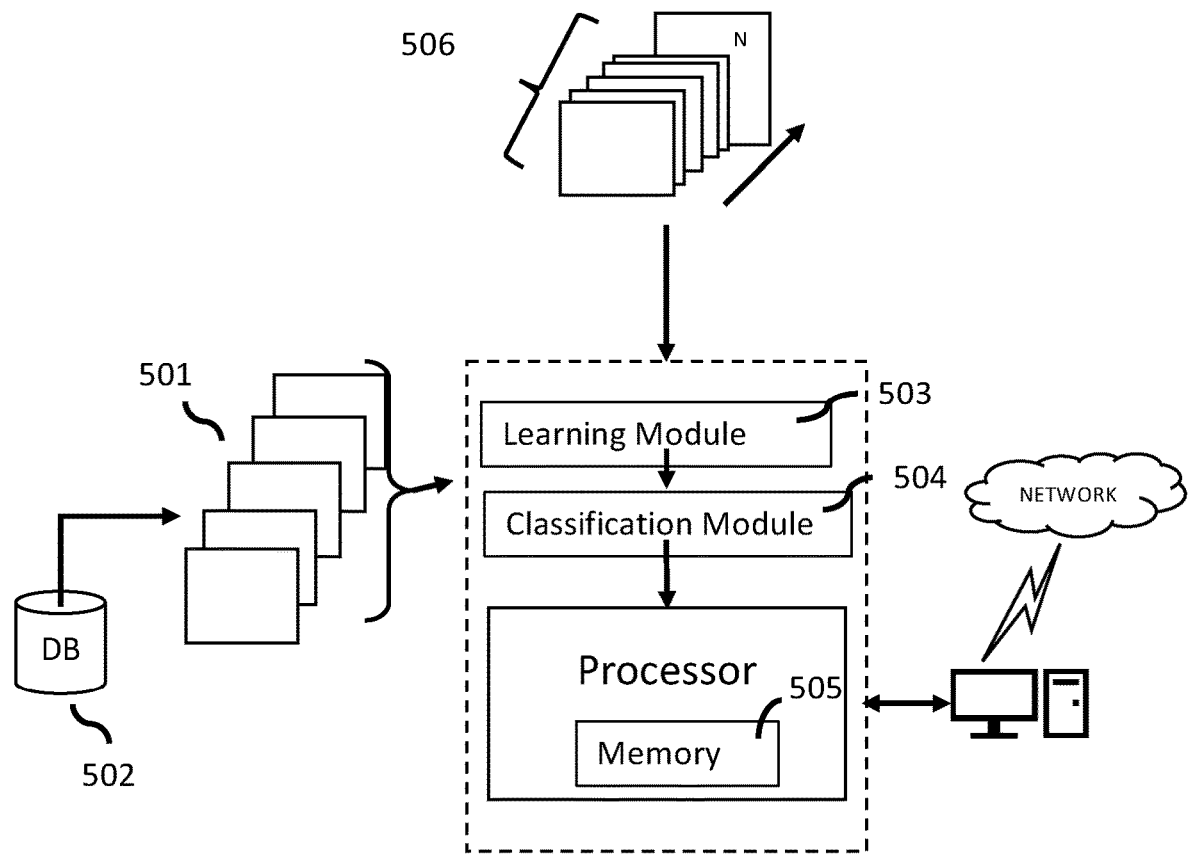

FIG. 11 provides high resolution micro-ultrasound images demonstrating some Indicator Features obtained in accordance with an embodiment of the invention;

FIG. 12 demonstrates an embodiment of a multiclass classifier of Indicator Features in high resolution micro-ultrasound images of prostate generated in accordance with an embodiment of the invention;

FIG. 13 provides high resolution micro-ultrasound images of prostate illustrating needle biopsy paths in accordance with an embodiment of the invention;

FIG. 14 is a block diagram of an exemplary computer system for implementing a method of generating Indicator Features in high resolution micro-ultrasound images of prostate and using them to generate a classifier and/or a multiclass classifier, in addition to use of the classifier to classify features in patient high resolution micro-ultrasound images of prostate according to an embodiment of this invention;

FIG. 15 provides an exemplary Possible Features Table illustrating a list of features and feature combinations along with number of cases where the feature was assigned and when the associated biopsy sample contained cancer. This data is used to determine the "Use for Training" column which states "Not Enough Data" for cases where only 1 example is available, and Unclear/Chance level if the ratio of N(Cancer)/N is sufficiently close to ½;

FIG. 16 is a flow diagram which illustrates one embodiment of the present method for assessing patient risk for prostate cancer in accordance with the teachings hereof;

FIG. 17 is a continuation of the flow diagram of FIG. 16 with flow processing continuing with respect to node B;

FIG. 18 is a block diagram of one example system for performing various aspects of the present method as described with respect to the flow diagrams of FIG. 16 and FIG. 17.

DETAILED DESCRIPTION

This invention provides a method of generating Indicator Features, Indicator Features and their use in a system comprising high resolution micro-ultrasound to determine a degree of risk for cancer in prostate tissue. Indicator Features are provided in high resolution micro-ultrasound images and are used to train a classifier, which can be used to determine a risk of cancer in other images, or can be grouped into a multiclass classifier, which can be used to determine a risk of cancer.

A Method of Generating Indicator Features

With conventional ultrasound, there was essentially only one feature available, a dark spot (hypoechoic region), which was used in the images as a possible indicator of cancer. As described in the Background, this feature correlated poorly with cancerous tissue. Thus, there was little confidence that ultrasound technology in general would be useful for identifying risk of cancer. Initially, once the prostate was able to be visualized with high resolution ultrasound, it was thought that the increased sensitivity would make the dark spot feature more reliable. Applying the traditional methodologies would have indicated that higher resolution imaging would reveal smaller dark spots, and this would be the feature to use in determining risk of cancer. This didn't work, however, indicating that the traditional way of looking for cancer using ultrasound did not work for the new high resolution systems.

With the advent of high resolution micro-ultrasound, significantly more detail, which is textural in nature in B-mode images was made available providing many possible features in the images. What was not known, however, was whether a subset of these newly identifiable patterns or features in these new high resolution images could be identified, characterized and tested to become reliable indicators of risk that cancer was absent or present in the tissue being imaged, especially given the failure of conventional ultrasound to do so. Moreover, given the high incidence of issues that commonly develop in an aging prostate, such as benign prostatic hyperplasia, which also exhibits abnormal but benign multiplication of the cells, or prostatitis, it was unknown whether these other disorders would exhibit similar features when imaged at a higher resolution that would only interfere with the ability to determine features reliably indicative of cancer.

What was needed by clinicians was a subset of features identifiable in high resolution ultrasound images that could be identified by clinicians and correlate with statistical significance and confidence to cancerous tissue. The number of features in this subset would need to be sufficiently large to be comprehensive, but not so large that a clinician would not be able to easily work with the list of possible indicator features when viewing an ultrasound image and making decisions while conducting a procedure of either examining a prostate for a risk of cancer or while conducting a biopsy to guide them to the tissue most likely at risk for cancer. Thus, what was needed in the art was a set of Indicator Features, which could be used by clinicians working with high resolution ultrasound systems that are indicative of benign tissue or tissue that has a very low risk of being cancerous.

High resolution micro-ultrasound image is an image which is generated using a high resolution micro-ultrasound transducer (15 MHZ or higher) to obtain electrical signals, which are then converted into an image. This image may be constituted in greyscale pixels (B-Mode), or may be rendered in color using known processing techniques such as Color Flow Imaging (Velocity or Power Doppler), Elastography, Contrast Enhancement, and/or Spectral Analysis. The scanning modality can be transrectal ultrasound (TRUS), transperineal, transabdominal, and/or intra surgery.

Overview of the Method for Generating Indicator Features

General Features would be any discernable, recurring patterns, or features, appearing in high-resolution micro-ultrasound images.

Possible Features are General Features, which are observed to correlate to tissue for which pathology is known, ranging from benign to the highest grade of cancer. Possible Features can be identified by using some form of Object-Based Image Analysis (OBIA), and are then characterized and given a useful label.

Candidate Features and/or combinations of Candidate Features will then be selected from the Possible Features (a useful Subset of Possible Features) and used to identify Possible Features and/or combinations thereof in a new set of training images for which the pathology is known but not provided to the reader of the image at the time of feature identification (reader blinded to the pathology). Candidate Features differ from Possible Features in that Possible Features could have a subjective bias as they were identified in the image while knowing the pathology of the corresponding tissue. Candidate Features are Possible Features which have been identified in tissue while the reader of the image was blinded to the pathology.

Candidate Features, which have been identified in a set of training images, will be used to populate a Candidate Feature Table and will be assigned the (blinded) pathology score. Additional patient data may be included in the Candidate Feature Table to generate an Augmented Feature Table. The Feature Table or Augmented Feature Table will be used to train a linear or non-linear classifier to determine the predictive probability of a Candidate Feature and/or combinations of Candidate Features being indicative of benign tissue or a grade of cancerous tissue. Candidate Feature and/or combinations of Candidate Features, which demonstrate little or no statistical significance, will be eliminated to yield Indicator Features Indicator Features are features appearing alone and/or in combination with other Indicator Features in high resolution micro-ultrasound images, which have been determined to be significantly statistically correlated to either benign tissue or some grade of cancerous tissue on the basis of predictive probabilities.

Figure 1:
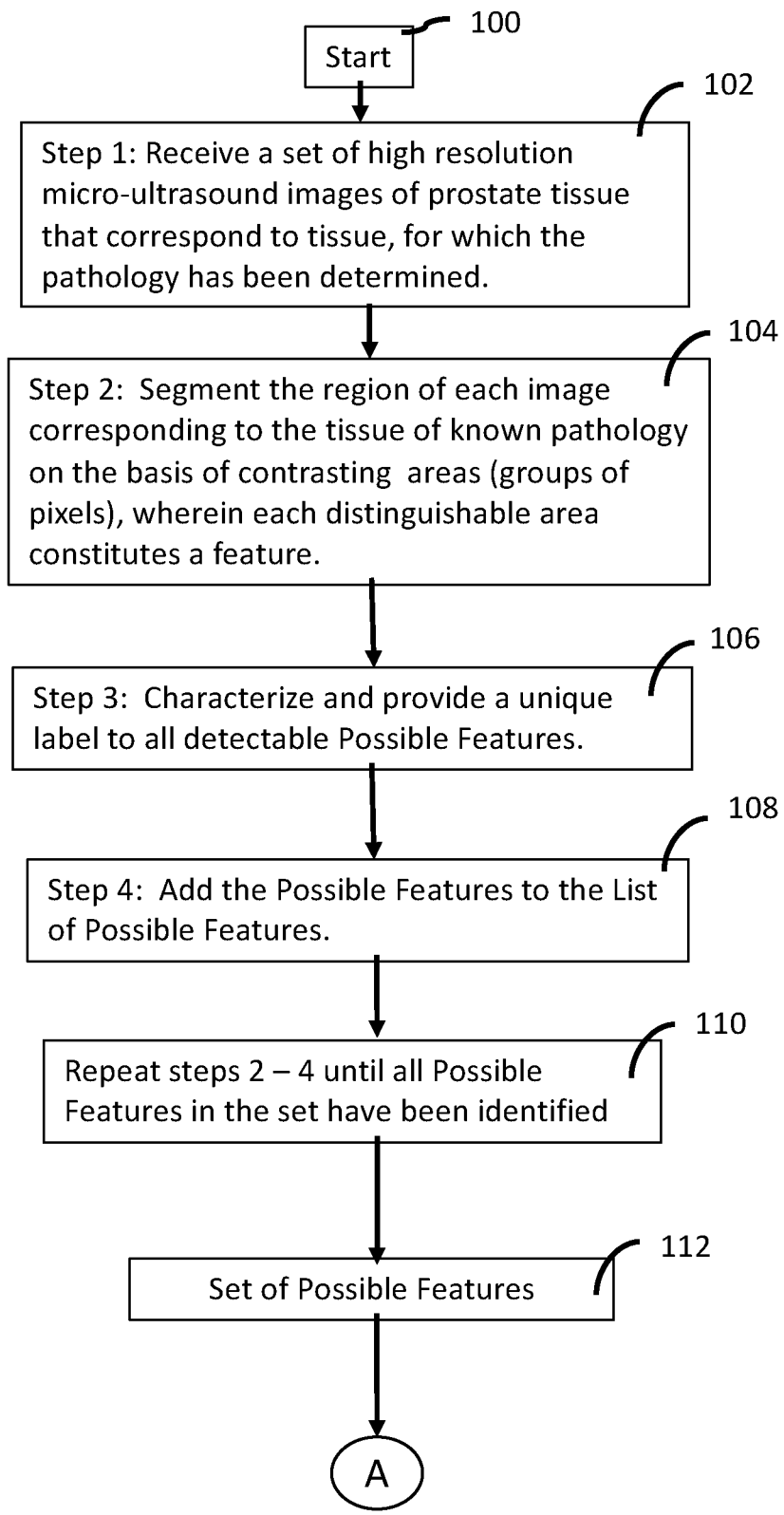
FIG. 1 is a flow diagram which illustrates one embodiment of the present method for generating indicator features in accordance with the teachings hereof.

Reference is now being made to the flow diagram of FIG. 1, which illustrates one embodiment of the present method for generating Indicator Features in accordance with the teachings hereof. Flow processing begins at step 100 and immediately proceeds to step 102. At step 102, receive a set of high resolution micro-ultrasound images of prostate tissue, which corresponds to tissue for which the pathology has been determined. At step 104, analyze the image to detect Possible Features by, for example, conducting some form of object-based image analysis (OBIA) in the areas of the image (groups of pixels) where the pathology of the tissue in the image is known. At step 106, characterize and provide a unique label to all detectable Possible Features. At step 108, add Possible Features thereby detected and/or combinations of Possible Features observed to occur together into the List of Possible Features. At step 110, repeat steps 104 through 108 until all Possible Features in the set have been identified to produce the Set of Possible Features at step 112.

Figure 2:
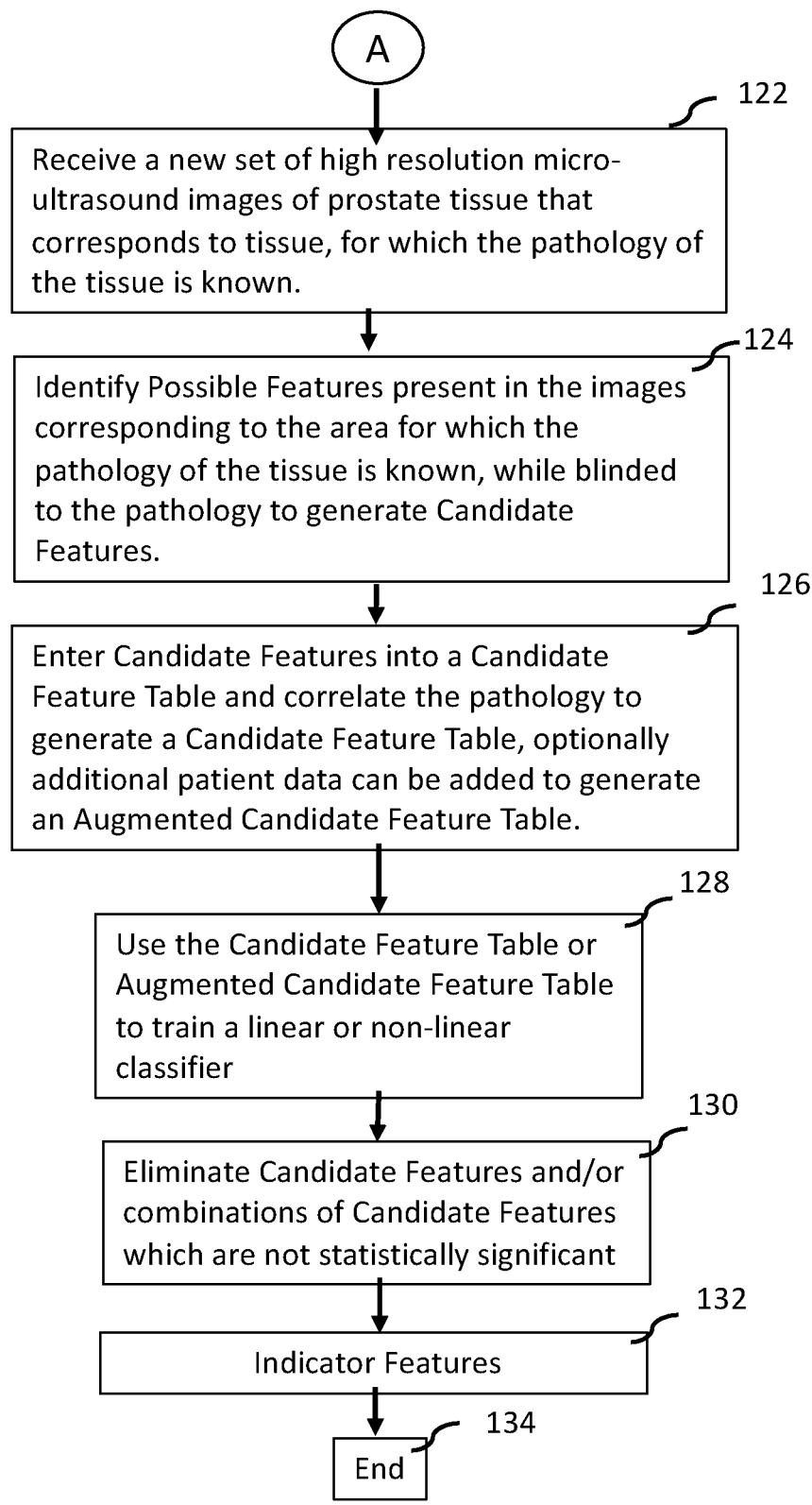
FIG. 2 is a continuation of the flow diagram of FIG. 1 with flow processing continuing with respect to node A.

Reference is now being made to the flow diagram of FIG. 2, which is a continuation of the flow diagram of FIG. 1, continuing with respect to node A. At step 122, obtain a set of high resolution micro-ultrasound images of prostate tissue that corresponds to tissue for which the pathology is known. It is possible to use the same training set but preferred to have a new set. At step 124, a reader identifies Possible Features present in the images corresponding to the area for which the pathology of the tissue is known, while blinded to the pathology to generate Candidate Features. At step 126, Enter Candidate Features into a Candidate Feature Table and correlate the pathology to generate a Candidate Feature Table, optionally additional patient data can be added to generate an Augmented Candidate Feature Table. At step 128, Use the Candidate Feature Table or Augmented Candidate Feature Table to train a linear or non-linear classifier. At step 130, eliminate Candidate Features and/or combinations of Candidate Features which are not statistically significant to produce a plurality of Indicator Features at step 132. If sufficient Indicator Features have been generated, then processing stops.

It should be appreciated that the flow diagrams depicted herein are illustrative. One or more of the operations may be performed in a different manner. Other operations may be added, modified, enhanced or consolidated. Variations thereof are intended to fall within the scope of the appended claims.

Indicator Features can then be used to generate an Indicator Feature Table, which can be used to train a classifier, which can then be used to classify future patient images. Additional patient data may be included in the Indicator Feature Table to generate an Augmented Indicator Feature Table. There are a number of algorithms known to one skilled in the art that can be used to analyze the Indicator Feature Table, which constitutes a training set to generate a predictive probability for the correlation between the presence of a feature in an image and the presence of cancer in the tissue being imaged. The classifier can be used to classify the features in images of patients generated using high-resolution micro-ultrasound devices.

Alternatively, these predicted probabilities can be used to create a multiclass classifier by grouping and ranking the features according to the similarities and differences between their weights or predicted probabilities. In this embodiment, the multiclass classifier can be used to classify the features in images of patients generated using high-resolution micro-ultrasound devices.

Figure 3:
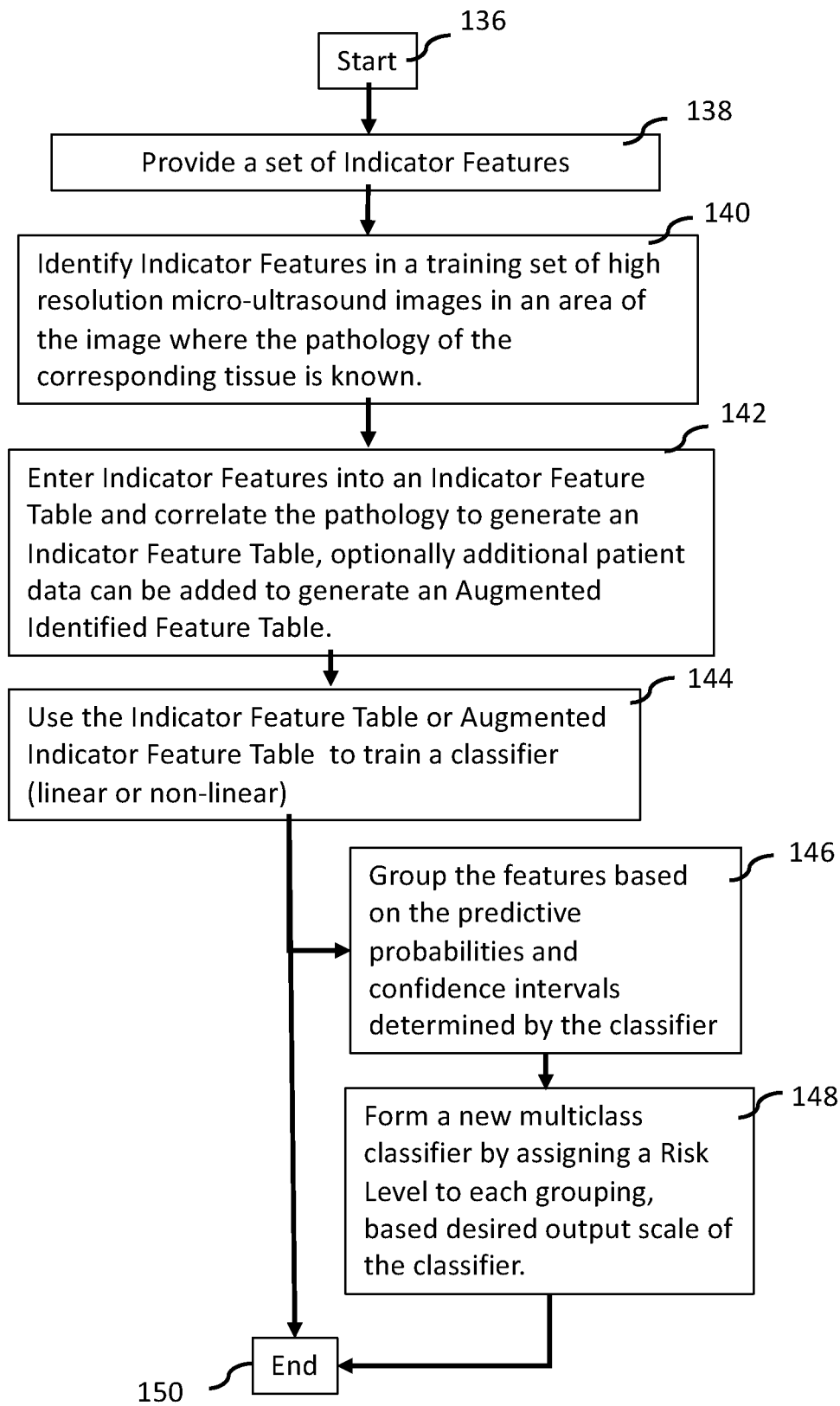
FIG. 3 is a flow diagram which illustrates a method for using Indicator Features to train a classifier and optionally a multiclass classifier in accordance with an embodiment of the invention.

Reference is now being made to the flow diagram of FIG. 3 which illustrates one embodiment of the present method for generating a classifier and/or multiclassifier comprising Indicator Features high resolution micro-ultrasound images. Flow processing begins at step 136 and immediately proceeds to step 138. At step 138, provide a set of Indicator Features. At step 140, identify Indicator Features in each of the training images in an area of the image where the pathology is known, but blinded to the reader. At step 142, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 144, the Indicator Feature Table or the Augmented Feature Table is used to train a linear or non-linear classifier. The process can stop here, or optionally, proceed to step 162, to group the features based on the predictive probabilities of each Indicator Feature and/or combination of Indicator Features. At step 148, form a new multiclass classifier based on the desired output scale of the classifier and the groupings of the features and the desired confidence intervals. The classifier or the multiclass classifier can be further trained using either the training data or test data.

High Resolution Micro-Ultrasound Images

The desired ultrasound for use with the disclosed methods can be applied, transmitted and received using an ultrasonic scanning device that can supply ultrasound at a center frequency sufficient to accurately resolve sonographic features on the order of 70 um. For example, a system with a center frequency transmit of at least about 15 MHz to the highest practical frequency can be used. In exemplary aspects, ultrasound can be supplied at a center frequency of 15 MHz, 16 MHz, 17 MHz, 18 MHz, 19 MHz, 20 MHz, 21 MHz, 22 MHz, 23 MHz, 24 MHz, 25 MHz, 26 MHz, 30 MHz, 31 MHz, 32 MHz, 35 MHz, 40 MHz, 45 MHz, 50 MHz, 55 MHz, 60 MHz, 65 MHz, 70 MHz, or higher than 70 MHz. Thus, an ultrasound system or device capable of operating at a center frequency at 15 MHz or above can be used.

One such exemplary system is the 29 MHz transrectal micro-ultrasound system and transducer (ExactVu™ micro-ultrasound, Exact Imaging, Toronto, Canada). Another such exemplary system can have the components and functionality described in U.S. Provisional Application No. 62/253, 310, which is incorporated herein by reference. Another exemplary system can have components and functionality described in PCT/IB2015/053458, which is incorporated herein by reference. Another such exemplary system can have components and functionality described in PCT/IB2015/052882, which is incorporated herein by reference.

It is contemplated that any system capable of producing an ultrasound image using a high frequency micro-ultrasound can be used. Thus, the methods can be practiced using a mechanically scanned ultrasound system that can translate an ultrasound beam as it sweeps along a path. The methods can also be practiced using an array based system where the beam is translated by electrical steering of an ultrasound beam along the elements of the transducer. One skilled in the art will readily appreciate that beams translated from either type system can be used in the described methods, without any limitation to the type of system employed. The type of system is therefore not intended to be a limitation to any described method because array and mechanically scanned systems can be used interchangeably to perform the described methods.

Needle Biopsy During Ultrasound Imaging

Embodiments described herein include a side-fire ultrasonic probe with an alignment feature that, when used to connect the probe to a needle guide for intra-cavity medical procedures, facilitates alignment of one or more needles translated through the needle guide with an imaging plane of an ultrasonic transducer. The alignment feature is configured such that alignment of a needle within the imaging plane is accomplished even when a protective sheath is disposed between the alignment feature and the needle guide.

By positioning the translated needles within the imaging plane of a side-fire type ultrasonic probe, an ultrasonic image can be used to image an advancing needle with respect to an intra-cavity structure of interest. This ability is particularly useful when the ultrasonic transducer has a frequency and/or resolution sufficient to image intra-structure or intra-organ features. Simultaneously imaging the structure of interest and the needle permits navigation of the needle to a specific intra-cavity structure within a human body, or, given sufficient resolution of the ultrasonic transducer, navigation of the needle to a specific location within the structure. This can then improve the diagnostic capability of the procedure or effectiveness of the therapy. Allowing for positioning of a needle oriented at different angles with respect to the probe enables access to a range of locations within the body or structure by the needles while reducing the manipulation of the probe. This can improve patient comfort during the procedure, as well as patient safety.

In an embodiment, an ultrasonic probe includes a cylindrical housing that includes a needle guide alignment feature on the surface of the housing. The alignment feature is used to connect a needle guide to the cylindrical housing and to align the needle guide such that a needle translated through the guide is translated in an imaging plane of the ultrasonic transducer. The alignment feature is configured such that the needle is aligned in the imaging plane even when a protective sheath is disposed between the housing and the needle guide. An exemplary needle guide alignment feature is provided by U.S. Pat. No. 9,113,825, incorporated by reference herein.

Generating a List of Possible Indicator Features

Possible Features are discernable, recurring patterns, or features, appearing in high-resolution micro-ultrasound images, which are observed to correlate to tissue for which pathology is known, ranging from benign to the highest grade of cancer. For example, the Gleason Sum scale ranges from Benign, 6, 7, 8, 9, & 10. Note that 2-5 used to be used as well but are generally now just labelled as benign. Other scales for grading the degree of cancer, or the stage of the cancer, in the tissue, though the concept remains the same. Possible Features are qualitative, not quantitative.

Possible Features can be identified by using some form of Object-Based Image Analysis (OBIA), which employs two main processes, segmentation and classification. Possible Features are then characterized and given a useful label. A label could be simply Feature A, Feature B, Feature C, etc. A label could be given a descriptive name that describes the texture present in the image that is somewhat intuitive such a "bright spot," or "mottled." This process is conducted for all the Possible Features that can be identified along the needle path of the biopsy needle or in a region corresponding to biopsied tissue.

Traditional image segmentation is on a per-pixel basis. However, OBIA groups pixels into homogeneous objects. These objects can have different shapes and scale. Objects also have statistics associated with them which can be used to classify objects. Statistics can include geometry, context and texture of image objects. Various systems have been developed for detecting and analyzing target patterns in digital images. A digital image is a rectangular array of pixels. Each pixel is characterized by its position in the array and a plurality of numerical pixel values associated with the pixel. The pixel values represent color information for various image layers. For example, grayscale digital images are represented by a single image layer, whereas RGB true-color images are represented by three image layers. Some existing analysis systems apply semantic networks to analyze the contents of the digital images. Systems that apply semantic networks perform object-oriented picture analysis, as opposed to solely statistical pixel-oriented analysis. Consequently, semantic network systems classify not only pixels, but also data objects linked to the pixels. The data objects that are linked to the pixels and to one another represent measurable information about the digital images.

Possible Features are identified by image segmentation in the region of the image corresponding to tissue, which has been biopsied. It is the process of determining areas (comprising groups of pixels) with similar image characteristics (e.g., color, intensity, texture) and which contrast to adjacent regions that are discernably different with respect to the same characteristic. For example, if the image is a greyscale image, an area (constituted by a group of pixels), which are almost white in color and appear adjacent to and surrounded by other areas, which are dark grey in color with a sharp contrast boundary between the two, the white area might be labelled a "bright spot." In another greyscale example, an area might appear light grey with "fuzzy" boundaries of slightly darker area, might be grouped together and labelled "mottled." Variations between areas may occur on a distinctive spatial scale (large or small areas of pixels), and may be described by relative changes in average brightness, sharpness and regularity of borders, and/or changes in gray-level textural parameters such as entropy, variability, contrast, or correlation. Regions with parameters different from typical normal tissue may be segmented and grouped based on these parameters.

In an embodiment, a human is used to generate the list of Potential Features. In an embodiment, a computer can be used to read the images and identify Possible Features and/or combinations of Possible Features in the images. In an embodiment, a human assisted by a computer can read the images and identify Possible Features and/or combinations of Possible Features in the images.

Exemplary Potential Features

In an embodiment, the first step entails determining distinguishable recurring patterns in high resolution transrectal micro-ultrasound images of prostate glands. In an embodiment, a 29 MHz transrectal micro-ultrasound system and transducer (ExactVu™ micro-ultrasound, Exact Imaging, Toronto, Canada) is used to acquire cine loops during each biopsy taken using the high resolution micro-ultrasound platform on patients who have had biopsies or radical prostatectomy such that clinical analysis data exists to determine whether the image correlates with cancerous tissue or not. The act of acquiring cine loops would be known to one skilled in the art as involving preparation of the transducer, insertion of the transducer into the rectum, adjustment of imaging settings to optimize image quality and through interrogation of the prostate gland to identify correct biopsy locations. These biopsy locations may be selected based on anatomy (biopsy of a particular region of the gland) or based on the sonographic features noted in the subject (targeted biopsy).

In an embodiment, whole-mount radical prostatectomy slides registered to micro-ultrasound images can be used as a starting point to suggest useful imaging features.

In an embodiment randomly-selected micro-ultrasound cine loops, each captured during one specific biopsy can be analyzed by one or more experts to determine imaging findings along the biopsy needle path indicative of carcinomas, as well as normal tissue.

In these embodiments at this stage of the process, the radical prostatectomy slides or biopsy data are not used to assign a link between a feature and cancerous tissue, but to assist in noticing which distinguishable and recurring aspects of the images might be suggestive or consistently present in tissue having a certain stage of prostate cancer.

In order to generate a list of ultrasound image features, a series of images or video cine loops can be reviewed by a series of experts to identify a large set of distinguishable, recurring features. Each reviewer assigns a term to any non-normal or non-uniform pattern encountered, then the reviewers meet to compare terms and select the most common nomenclature for each feature. In an embodiment, text descriptions may be analyzed by a computer using natural language processing systems to extract these features.

In an embodiment, a series of still images and/or cine loops can be analyzed by a computer for pattern detection to determine a list of distinguishable and recurring features existing in the images, presenting potential candidate features which might be found to be consistently able to be correlated to a stage or risk of prostate cancer.

In an embodiment, the Possible Features comprise features having the same or similar characteristics as:

| Feature |
| --- |
| Heterogenous-Bright Echoes-Finger/Funky Shadows |
| Heterogenous-Finger/Funky Shadows |
| Heterogenous-Coarse-Shadows |
| Heterogenous-Hyperechoic-Coarse |
| Heterogenous-Irregular |
| Heterogenous-Lesion |
| Heterogenous-Coarse-Finger/Funky Shadows |
| Heterogenous-Irregular-Coarse |
| Heterogenous-Shadows |
| Heterogenous-Defined |
| Heterogenous-Defined-Coarse |
| Heterogenous-Hyperechoic |
| Heterogenous-Hyperechoic-Irregular |
| Heterogenous-Hypoechoic-Lesion-Bright Echoes |
| Heterogenous "Cauliflower" |
| Heterogenous "Smudged" |
| Heterogenous "Mottled" |
| Heterogenous "Cauliflower/Smudgy/Mottled" |
| Mild Heterogeneity |
| Bright Echoes |
| Bright Echoes in Hyperechoic Tissue |
| Mixed Echo Legions |
| Hyperechoic-Coarse-Shadows |
| Hyperechoic-Hypoechoic-Defined |
| Hyperechoic-Hypoechoic-Lesion-Bright Echoes |
| Hyperechoic With or Without Ductal Patches |
| Hypoechoic |
| Hypoechoic-Bright Echoes-Coarse |
| Heterogenous-Bright Echoes-Coarse |

| Feature |
| --- |
| Heterogenous-Bright Echoes |
| Heterogenous-Coarse |
| Hyperechoic-Hypoechoic-Lesion-Coarse |
| Hypoechoic-Defined |
| Hyperechoic-Bright Echoes-Coarse |
| Anechoic-Heterogenous-Defined |
| Heterogenous |
| Heterogenous-Hypoechoic-Lesion-Coarse |
| Hyperechoic-Coarse-Irregular Prostate Borders |
| Hyperechoic-Coarse-Microgranulomas |
| Hyperechoic-Hypoechoic-Bright Echoes |
| Hyperechoic-Hypoechoic-Lesion |
| Hypoechoic-Lesion-Bright Echoes-Coarse |
| Hypoechoic-Undefined/Vague |
| Hyperechoic-Hypoechoic |
| Hyperechoic-Bright Echoes |
| Hyperechoic-Coarse |
| Anechoic-Hyperechoic-Defined |
| Hyperechoic |
| Irregular Prostate (PZ) |
| Irregular Prostate Boarder |
| Bright Echoes |
| Bright Echoes-Coarse |
| Coarse |
| Heterogenous-Hyperechoic-Lesion |
| Coarse-Small Ducts |
| Small Ducts |
| Small regular ducts "Swiss cheese" |

Generating a Set of Candidate Features

According to an embodiment, the Possible Features are then further processed by having someone skilled in the art of reading images, a computer or a combination thereof, identify the presence or absence of a Possible Features in a set of new training images, but blinded to the pathology while recording the presence or absence of features along the path of the biopsy needle in the image. Only features that overlap with the biopsy path are used. Any of the Possible Features that are assigned to images in the new training set are now considered Candidate Features. Since the individual is blinded to the pathology of the biopsy results, this step accounts for possible subjective interpretation biases of the features by the individual. If combinations of features are observed to occur together, then combinations can be included and treated as a singular feature, ie., when the individual features are present alone, then they are treated as one piece of data, but when the features are present together, they are treated both as one piece of data and also recorded as individual features.

Then the results are used to construct a Candidate Feature Table, where they are correlated to the actual pathology of the tissue imaged in the region where the Candidate Feature was identified.

In an embodiment, similar steps are followed to identify the images, but whole-mount radical prostatectomy slides registered to micro-ultrasound images can be used to further process the Set of Candidate Indicator Features.

In an embodiment, a computer can be used to read the images and identify Candidate Features and/or combinations of Candidate Features in the new training set of images.

In another embodiment, other patient data is analyzed along with the features (with or without biopsy data), to increase the confidence that a specific feature is associated with cancer, comprising data obtained from: spatial information about the image, spatial information about the features, 3-D information, spectral information about the image, and, images collected using other modalities such as B-mode (grey-scale), Velocity Color Flow Imaging, Power Doppler Color Flow Imaging, Elastography, Contrast Enhanced Ultrasound, Spectral Analysis, conventional resolution ultrasound, MRI, CT, or PET imaging, patient age, DRE results, PSA readings, free PSA, PSA density, family history, race, prostate volume, transition zone volume, relevant biomarkers, protein/hormonal biomarker levels, genetic screening results, or number of prior negative biopsies This additional information is then included in the Augmented Candidate Feature Table along with each feature or combination of features.

| Feature | N(F present) | N(Cancer - biopsy) |
|---|---|---|
| A | | |
| B | | |
| A + B | | |
| C | | |
| D | | |
| A + D | | |

| Augmented Patient Data | Mean Value | Mean Value (Cancer biopsy) |
|---|---|---|
| PSA | | |
| Doppler Value | | |
| Elastography Value | | |

Candidate Feature and/or combinations of Candidate Features, which demonstrate little or no statistical significance will be eliminated to yield Indicator Features. One skilled in the art would appreciate that the range of the confidence interval on predictive probability spanning 1 (equivalent risk of benign or cancerous tissue) constitutes the threshold of statistical significance.

An Exemplary Set of Candidate Features

Using the Possible Features, Candidate Features can be identified in new set of training images, for which the pathology is known, but blinded to the reader of the images.

In an embodiment, a set of Possible Features to be used to identify Candidate Features comprise features having the same or similar characteristics as
 a) small regular ducts "Swiss cheese"
 b) hyperechoic with or without ductal patches
 c) mild heterogeneity
 d) bright echoes in hyperechoic tissue
 e) heterogeneous "cauliflower/smudgy/mottled" appearance
 f) bright echoes
 g) irregular prostate (PZ)
 h) irregular prostate border
 i) mixed-echo lesions
 j) irregular shadowing In an embodiment, a set of Possible Features to be used to identify Candidate Features comprise features having the same or similar characteristics as:
 a) regular ductal pattern "Swiss cheese";
 b) hyperechoic with ductal patches;
 c) mild heterogeneity with small bright echoes in hyperechoic tissue;
 d) bright echoes;
 e) heterogeneous "smudged/mottled";
 f) heterogeneous "cauliflower";
 g) irregular shadowing; and
 h) mixed echo lesion causing irregular prostate borders.

For example, in an embodiment 200 randomly-selected micro-ultrasound cine loops, each captured during one specific biopsy (from a total of 121 patients), can be analysed by one or more experts to determine imaging findings along the biopsy needle path indicative of high grade (Gleason Sum greater than 7) and low-intermediate grade (Gleason Sum 7 or less) carcinomas, as well as normal tissue. For example, the sample set can include 100 benign, 50 low-grade and 50 high-grade biopsy-proven samples. In an embodiment, experts can be blinded to the pathological findings of each biopsy sample, and record the variety of Potential Features present along the needle path in each image, which once identified (blinded) become Candidate Features. These Candidate Features can then be analyzed to see how often they are associated with biopsy-proven benign tissue or cancer.

In another embodiment, other information is analyzed along with the features (with or without biopsy data), to increase the confidence that a specific feature is associated with cancer, comprising, with additional data pertaining to the patient based on data obtained from: B-mode (grey-scale) images, Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies.

TABLE 1

An exemplary Candidate Feature Table comprising a list of sonographic features for which biopsy results are attributed.

| Feature | N (Total) | N (Cancer) |
|---|---|---|
| Small regular ducts "Swiss cheese" | 7 | 1 |
| Hyperechoic, with or without ductal patches | 50 | 14 |
| Mild heterogeneity | 42 | 24 |
| Bright Echoes in hyperechoic tissue | 10 | 4 |
| Heterogeneous "cauliflower/smudgy/mottled" appearance | 32 | 22 |
| Bright Echoes | 30 | 18 |
| Irregular Prostate (PZ) | 1 | 1 |
| Irregular PZ border | 1 | 1 |
| Mixed-echo lesions | 2 | 2 |
| Irregular Shadowing | 12 | 11 |

Determining a Risk Parameter for Each Candidate Feature or Combination of Candidate Features There are various statistical univariate and multivariate methodologies that can be used to assign a Risk Parameter to each sonographic feature presented in the Pathology Set of Pathology Training Features. The objective is to determine when a feature is present in a sonographic image, what is the probability that it is associated with the tissue being imaged having a grade of prostate cancer versus benign tissue.

Expressed in terms of predictive analytics, the pathological diagnosis is the dependent variable, the sonographic feature (abnormality) is the independent variable and the mathematical task is to ascertain the likelihood that the presence of the independent variable (the sonographic feature) is dependent upon the presence of cancer in that tissue. The answer can be binomial in that the equation seeks to prove either cancer is present or absent with each feature. Alternatively, the answer may be expressed as a beta random variable, expressing the increased or decreased risk of cancer on a continuous scale between 0 (no risk) and 1 (certainty of cancer). This continuous scale may also be expressed as an odds ratio or relative risk between 0 (no risk) and infinity (certainty of cancer).

In an embodiment, a univariate relative risk (RR) and a confidence interval (CI) are calculated for each sonographic feature, and used to assign a risk parameter to each Candidate Feature and/or combination of Candidate Features. Candidate Features and/or combinations of Candidate Features which do not demonstrate sufficient statistical significance will be eliminated to generate the Indicator Features.

Indicator Features

Indicator Features are features appearing alone and/or in combination with other Indicator Features in high resolution micro-ultrasound images, which have been determined to be significantly statistically correlated to either benign tissue or some grade of cancerous tissue on the basis of predictive probabilities.

Indicator Features can then be used to generate an Indicator Feature Table, which can be used to train a classifier, which can then be used to classify future patient images. There are a number of algorithms known to one skilled in the art that can be used to analyze the Indicator Feature Table, which constitutes a training set to generate a predictive probability for the correlation between the presence of a feature in an image and the presence of cancer in the tissue being imaged. The classifier can be used to classify the features in images of patients generated using high-resolution micro-ultrasound devices.

Alternatively, these predicted probabilities can be used to create a multiclass classifier by grouping and ranking the features according to the similarities and differences between their weights or predicted probabilities. In this embodiment, the multiclass classifier can be used to classify the features in images of patients generated using high-resolution micro-ultrasound devices.

Exemplary Indicator Features

In an embodiment, the Indicator Features comprise features having the same or similar characteristics as
   (a) small regular ducts "Swiss cheese;"
   (b) regular ductal pattern "Swiss cheese";
   (c) hyperechoic with ductal patches;
   (d) hyperechoic with or without ductal patches;
   (e) mild heterogeneity with small bright echoes in hyperechoic tissue;
   (f) mild heterogeneity;
   (g) bright echoes in hyperechoic tissue;
   (h) heterogeneous "smudged/mottled";
   (i) heterogeneous "cauliflower";
   (j) heterogeneous "cauliflower/smudgy/mottled" appearance;
   (k) bright echoes;
   (l) irregular prostate (PZ);
   (m) irregular prostate border;
   (n) mixed-echo lesions;
   (o) irregular shadowing; or
   (p) mixed echo lesion causing irregular prostate borders.

A set of Indicator Features can then be used to generate an Indicator Feature Table. In an embodiment, this is generated by re-using the data that used to evaluate the Candidate Features (for which the statistically insignificant Candidate Features have now been removed). The Table can be used to train a classifier, which can then be used to classify future patient images. The results of this classifier can optionally be grouped to generate a multiclass classifier, which then can be used to classify future patient images.

In an embodiment, a new set of images (for which the pathology is known) can be used to identify Indicator Features in the images, while blinded to the pathology, then use the results of assigning Indicator Features to the new set of images plus the corresponding pathology to populate an Indicator Feature Table. Optionally, additional patient data can be included in the Table. The Table can be used to train a classifier, which can then be used to classify future patient images. The results of this classifier can optionally be grouped to generate a multiclass classifier, which then can be used to classify future patient images.

In an embodiment, a set of Indicator Features comprise features having the same or similar characteristics as:
   a) small regular ducts "Swiss cheese"
   b) hyperechoic with or without ductal patches
   c) mild heterogeneity
   d) bright echoes in hyperechoic tissue
   e) heterogeneous "cauliflower/smudgy/mottled" appearance
   f) bright echoes
   g) irregular prostate (PZ)
   h) irregular prostate border
   i) mixed-echo lesions
   j) irregular shadowing In an embodiment, a set of Indicator Features comprise features having the same or similar characteristics as:
   a) regular ductal pattern "Swiss cheese";
   b) hyperechoic with ductal patches;
   c) mild heterogeneity with small bright echoes in hyperechoic tissue;
   d) bright echoes;
   e) heterogeneous "smudged/mottled";
   f) heterogeneous "cauliflower";
   g) irregular shadowing; and
   h) mixed echo lesion causing irregular prostate borders.

In another embodiment, other patient data is analyzed along with the features (with or without biopsy data), to increase the confidence that a specific feature is associated with cancer, comprising data obtained from, B-mode (greyscale) images, Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies.

This additional information is then included in an Augmented Indicator Feature Table along with each feature or combination of features.

| Feature | N(F present) | N(Cancer - biopsy) |
|---|---|---|
| A | | |
| B | | |
| A + B | | |
| C | | |
| D | | |
| A + D | | |

| Augmented Patient Data | Mean Value | Mean Value (Cancer biopsy) |
|---|---|---|
| PSA | | |
| Doppler Value | | |
| Elastography Value | | |

In an embodiment, a training set comprising Indicator Features, which have been correlated to clinical pathology data for the same tissue imaged in the sonogram. In an embodiment, this is accomplished by using a high-resolution transrectal micro-ultrasound system to acquire images of the needle path followed during each biopsy taken on patients. The pathological analysis of the tissue collected in each biopsy is then used determine image findings (features) along the biopsy needle path indicative of carcinomas, as well as normal tissue.

In an embodiment, a univariate relative risk (RR) and a confidence interval (CI) are calculated for each sonographic feature, and used to assign a risk parameter to each Indicator Feature and/or combination of Indicator Features.

Figure 4:
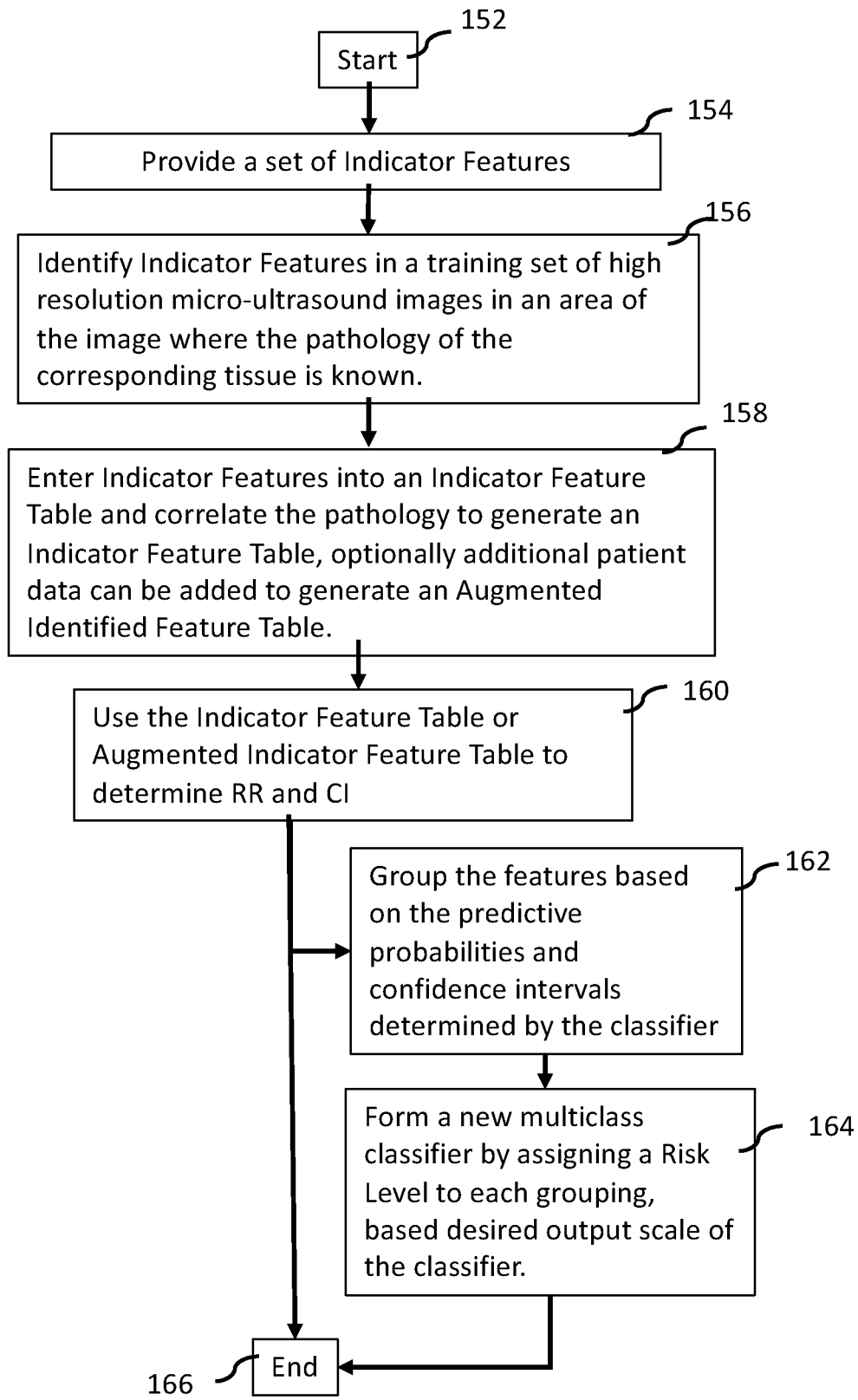
FIG. 4 is a flow diagram which illustrates a method for using Indicator Features to determine relative risk (RR) and a confidence interval (CI) and optionally generate a multiclass classifier in accordance with an embodiment of the invention.

In another embodiment, the calculating step uses machine learning. Common machine learning algorithms may be used to create a classifier based on the feature data, such as binary classification trees, "random forests", support vector machines, artificial neural networks, and naïve bayesian networks. In another embodiment, multivariate relative risk is calculated for a combination of features. A skilled person would understand as the number of features increases machine learning is used since the complexity of selecting appropriate thresholds and managing generalizability increases exponentially with the number of features or combination of features Calculating a Univariate RR and CI for Each Indicator Feature and/or Combination of Indicator Features FIG. 4 illustrates the process of building a multiclass classifier calculating a univariate relative risk (RR) and a confidence interval (CI) for each sonographic feature, and used to assign a risk parameter to each sonographic feature in the Indicator Features Table, which can be then used to generate a multiclass classifier. The RR ratio is the relative occurrence of a given feature or symptom in two distinct populations. In other words, the RR for each sonographic feature indicates the relative occurrence of each feature in a population of cancerous tissue versus non-cancerous tissue. Large differences in occurrence rates suggest that the feature may be used to predict which population a given image or patient belongs to. Equation (1) is used to calculate a relative risk ratio (Table 2) of each Indicator Feature.

TABLE 2

Example variables for Relative Risk Ratio Calculation

|  | Disease Present | Disease Absent |
|---|---|---|
| Feature Present | A | B |
| Feature Absent | C | D |

$$RR = \frac{A}{A+B} \bigg/ \frac{C}{C+D} \quad (1)$$

The statistical significance of this ratio may be approximated by assuming a log-normal distribution with mean ln(RR) and variance given in Equation 2.

$$\sigma^2 = \frac{B}{A(A+B)} + \frac{D}{C(C+D)} \quad (2)$$

So that the 95% confidence interval may be calculated by:

$$CI = e^{m \pm 1.96\sigma} \quad (3)$$

Table 3 illustrates relative risks (RR) and confidence intervals (CI) calculated for example Indicator Features from blinded analysis of 100 biopsy-proven benign and 100 biopsy-proven malignant cine loops

| Indicator Features | N (Total) | N (Cancer) | RR [90% CI] |
|---|---|---|---|
| Small regular ducts "Swiss cheese" | 7 | 1 | 0.28 [0.05-1.72] |
| Hyperechoic, with or without ductal patches | 50 | 14 | 0.49 [0.31-0.78] |
| Mild heterogeneity | 42 | 24 | 1.19 [0.87-1.62] |
| Bright Echoes in hyperechoic tissue | 10 | 4 | 0.79 [0.37-1.71] |
| Heterogeneous "cauliflower/smudgy/mottled" appearance | 32 | 22 | 1.48 [1.11-1.97] |
| Bright Echoes | 30 | 18 | 1.24 [0.89-1.73] |
| Irregular Prostate (PZ) | 1 | 1 | 2.01 [1.75-2.31] |
| Irregular PZ border | 1 | 1 | 2.01 [1.75-2.31] |
| Mixed-echo lesions | 2 | 2 | 2.02 [1.76-2.33] |
| Irregular Shadowing | 12 | 11 | 1.94 [1.54-2.43] |

Note that in this example, no correction was made to account for the number of features tested. Such a correction is warranted and would likely widen the 95% confidence intervals, but should not affect the ranking of features.

Building a Multiclass Classifier

Reference is now being made to the flow diagram of FIG. 4 which illustrates one embodiment of the present method for generating a classifier comprising high resolution ultrasound images. Flow processing begins at step 152 and immediately proceeds to step 154. At step 154, provide a set of Indicator Features. At step 156, identify Indicator Features in each of the training images in an area of the image where the pathology is known, but blinded to the reader. At step 158, the pathology data is linked to the sonographic features because the tissue sample and training image are taken from the same physical location in the prostate. At step 160, a univariate relative risk and a confidence interval are calculated for each sonographic feature or group of features. At step 162, group the features based on the relative risk and the confidence interval of each individual feature. At step 164, form a new multiclass classifier based on the desired output scale of the classifier and the groupings of the features and the desired confidence intervals.

Grouping Features to Build a Multiclass Classifier

In an embodiment using a relative risk and confidence interval classifier, the singular features are grouped based on the relative risk and confidence interval of each individual feature. If a linear classifier is used, combinations of features may also be added if sufficient data is available. A new multiclass classifier is formed based on the desired output scale of the classifier and the groupings of the features and the desired confidence intervals.

In an embodiment, predefined thresholds are used to group features based on mean relative risk values. For a data set with balanced numbers of cancerous and benign observations, these predetermined values split the theoretical 0-2 range of the relative risk value into sections that provide useful assessment of the underlying risk, for example:

| Risk Score | Mean RR Range | Assignment |
|---|---|---|
| 1 | 0-0.4 | Very low risk |
| 2 | 0.4-0.6 | Some risk |
| 3 | 0.6-1.2 | Indeterminate risk |
| 4 | 1.2-1.6 | Significant risk |
| 5 | 1.6+ | Very High risk |

In an embodiment, automated thresholding is used to determine the output scale. The following procedure may be used:

1. The pair of values with closest mean RR are chosen and their CI ranges compared. If the CI ranges overlap by a certain percentage, the values are combined. The new mean for the group is taken as the mean of the component RR values, and the CI as the intersection of the individual CI ranges.
2. Step 1 is repeated until no further merges are possible.
3. Steps 1 and 2 are repeated for the pair of values with the second closest mean RR values, etc. Until every pair has been checked without a merge.
4. The resulting groups are sorted by their mean RR values and assigned Risk Scores from 1 (lowest RR) to N (highest RR). The overlap percentage may be adjusted to give a desirable number of classes for training purposes.

Alternatively, k-nearest neighbors clustering may be used with a fixed number of predefined starting classes spaced evenly over the RR space.

In an embodiment, the point scale may be less than 5 points. In an embodiment, the point scale may be 5 points. In an embodiment, the point scale may be 6 points. In an embodiment, the point scale may be 7 points. In an embodiment, the point scale may be 8 points. In an embodiment, the point scale may be 9 points. In an embodiment, the point scale may be 10 points. In an embodiment, the point scale may be more than 10 points.

In an embodiment, the point scale may include sub classifications. For example, the point scale is 1, 2, 3A, 3B, 3C, 4, 5.

In an embodiment, the machine learning analysis is used to rank and group features with similar risk profiles into an easy to use point scale.

Table 4 illustrates how the RR and CI results can be used to group and assign a Risk Score to the Indicator Features, thereby creating a multiclass classifier for high resolution micro ultrasound sonograms of the prostate.

| Feature | N (Total) | N (Cancer) | RR [90% CI] | Assigned Risk Score |
|---|---|---|---|---|
| Small regular ducts "Swiss cheese" | 7 | 1 | 0.28 [0.05-1.72] | 1 |
| Hyperechoic, with or without ductal patches | 50 | 14 | 0.49 [0.31-0.78] | 2 |
| Mild heterogeneity | 42 | 24 | 1.19 [0.87-1.62] | 3 |
| Bright Echoes in hyperechoic tissue | 10 | 4 | 0.79 [0.37-1.71] | 3 |
| Mild heterogeneity + Bright Echoes in hyperechoic tissue | | | | 4 |
| Heterogeneous "cauliflower/smudgy/mottled" appearance | 32 | 22 | 1.48 [1.11-1.97] | 4 |
| Bright Echoes | 30 | 18 | 1.24 [0.89-1.73] | 4 |
| Irregular Prostate (PZ) | 1 | 1 | 2.01 [1.75-2.31] | 5 |
| Irregular PZ border | 1 | 1 | 2.01 [1.75-2.31] | 5 |
| Mixed-echo lesions | 2 | 2 | 2.02 [1.76-2.33] | 5 |
| Irregular Shadowing | 12 | 11 | 1.94 [1.54-2.43] | 5 |

In an embodiment, the multiclass classifier comprises a possible risk level of:
1. 1 (very low) for small regular ducts "Swiss cheese" with no other heterogeneity or bright echoes;
2. 2 (some) for hyperechoic, with or without ductal patches (possible ectatic glands or cysts);
3. 3 (indeterminate) for mild heterogeneity or bright echoes in hyperechoic tissue;
4. 4 (significant) for heterogeneous "cauliflower/smudgy/mottled" appearance or bright echoes (possible comedonecrosis); and
5. 5 (very high) for irregular shadowing (originating within the prostate, not the prostate border) or mixed-echo lesions or irregular prostate and/or PZ border In an embodiment, the multiclass classifier comprises a risk level of:
1. 1 (very low) for small regular ducts or "Swiss Cheese" feature;
2. 2 (some) for hyperchoic with/without ductal patches features;
3. 3 (indeterminate) for a mild heterogeneity or bright echoes in hyperechoic tissue;
4. 4 (significant) for heterogeneous "cauliflower, smudgy or mottled" or bright echoes "starry sky" features; and
5. 5 (very high) for irregular shadowing or mixed-echo lesions or irregular prostrate/PZ border.

Linear and Non-Linear Classifiers

In an embodiment, RR and CI results are used to generate predictive probabilities for Indicator Features. One skilled in the art, however, would appreciate that it would therefore be possible to using an alternative mathematical processing, such as binary classification trees, "random forests", support vector machines, artificial neural networks, and naïve bayesian networks, of the same results found in the Indicator Feature Table or Augmented Indicator Feature Table. In all of these cases each Indicator Feature and/or combination of Indicator Features is considered as a separate column of a feature matrix, which may take on Boolean values (present or absent). One row of this matrix is created for each image/cine loop (biopsy sample) available. Pathological result is also modelled as a boolean value in the form of a vector with one entry per image/cine loop (biopsy sample) indicating the presence or absence of cancer.

Binary Classification Trees

Figure 5:
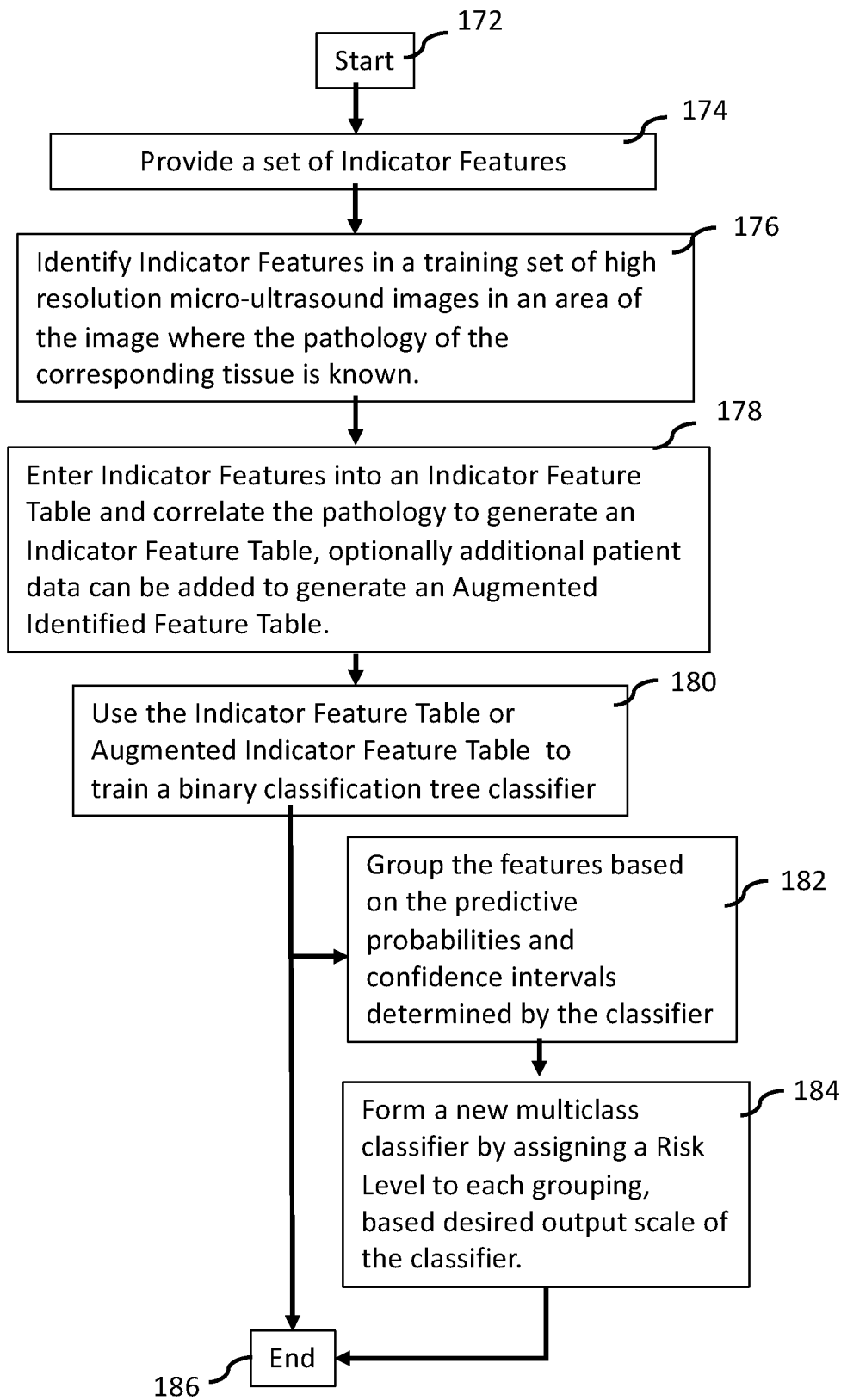
FIG. 5 is a flow diagram which illustrates a method for using Indicator Features to train a binary classification tree classifier and optionally a multiclass classifier in accordance with an embodiment of the invention.

Reference is now being made to the flow diagram of FIG. 5 which illustrates one embodiment of the present method for generating a classifier and/or multiclassifier comprising Indicator Features high resolution micro-ultrasound images. FIG. 5 illustrates the process of training a binary classification tree classifier using an Indicator Feature Table or Augmented Indicator Feature Table. Flow processing begins at step 172 and immediately proceeds to step 174. At step 174, provide a set of Indicator Features. At step 176, identify Indicator Features in each of the training images in an area of the image where the pathology is known, but blinded to the reader. At step 178, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 180, the Indicator Feature Table or the Augmented Feature Table is used to train a binary classification tree classifier. The process can stop here at step 186, or optionally, proceed to step 182, to group the features based on the predictive probabilities of each Indicator Feature and/or combination of Indicator Features. At step 184, form a new multiclass classifier based on the desired output scale of the classifier and the groupings of the features and the desired confidence intervals. Optionally, the classifier or the multiclass classifier can be further trained using either training data or test data.

A binary classification tree may be created using the following algorithm:

For each Indicator Feature, split the dataset based on the presence or absence of the feature.
(a) Calculate a purity measure such as deviance, or Gini's diversity (b) Select the feature that leads to the split with the highest purity and create two daughter nodes, one with the presence of the feature and one with the absence For each daughter node, (a) If the size of the daughter node is above a threshold N entries (determined by one skilled in the art based on the size of the dataset, for example 10), repeat 1 and 2 iteratively on the node.

(b) If the size of the daughter node is below the threshold N, stop.

The classifier is queried by starting at the root node and following each branch based on the input until a "leaf" or terminal node is reached. One may use the ratio of positive cases at the terminal node as the output. For example, if a terminal node contained 3 benign and 7 cancerous cases the output would be 70%.

Random Forests

Figure 6:
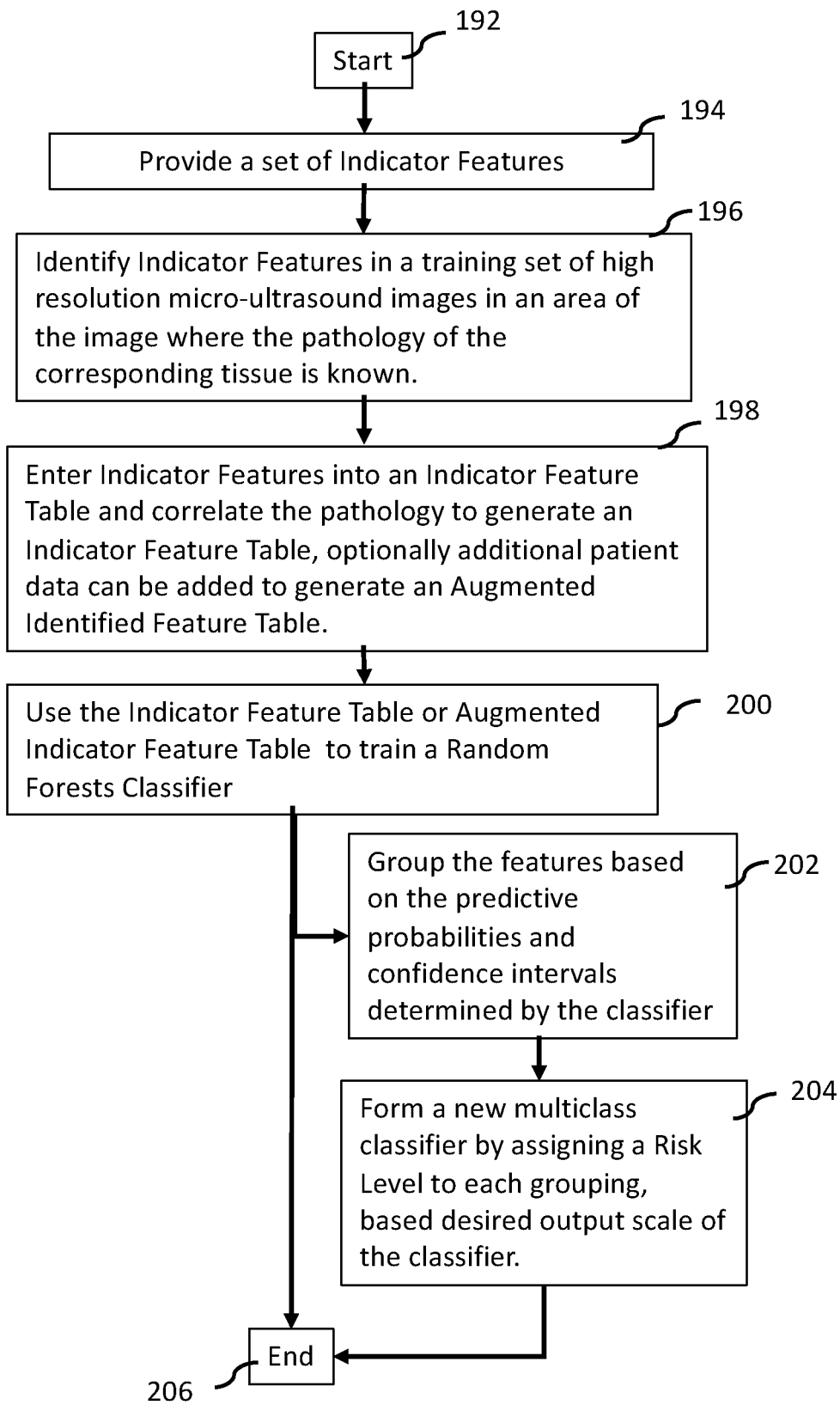
FIG. 6 is a flow diagram which illustrates a method for using Indicator Features to train a random forests classifier and optionally a multiclass classifier in accordance with an embodiment of the invention.

Reference is now being made to the flow diagram of FIG. 6, which illustrates one embodiment of the present method for generating a classifier and/or multiclassifier comprising Indicator Features high resolution micro-ultrasound images. FIG. 6 illustrates the process of training a random forest classifier using an Indicator Feature Table or Augmented Indicator Feature Table. Flow processing begins at step 192 and immediately proceeds to step 194. At step 194, provide a set of Indicator Features. At step 196, identify Indicator Features in each of the training images in an area of the image where the pathology is known, but blinded to the reader. At step 198, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 200, the Indicator Feature Table or the Augmented Feature Table is used to train a random forest classifier. The process can stop here at step 206, or optionally, proceed to step 202, to group the features based on the predictive probabilities of each Indicator Feature and/or combination of Indicator Features. At step 204, form a new multiclass classifier based on the desired output scale of the classifier and the groupings of the features and the desired confidence intervals. Optionally, the classifier or the multiclass classifier can be further trained using either training data or test data.

A random forest classifier may be created using the following algorithm:

Randomly select a subset of the data (X %, where X may be selected by one skilled in the art based on the size of the available dataset, in general X<90%)

Follow the procedure for generating a Binary Classification Tree based using this subset Save the resulting tree, and repeat from step 1 N times to produce N distinct classification trees (where N may be selected by one skilled in the art based on the size of the available dataset, in general N>100)

The classifier is queried by querying each individual tree with a given input, and taking the average response of the set of trees. For example, for the input case "Bright echoes AND irregular border" the trees may range in suspicion of cancer from 70-90%, one might report the outcome as having a mean value of 80% with a confidence interval of 72-85%.

Support Vector Machines

Figure 7:
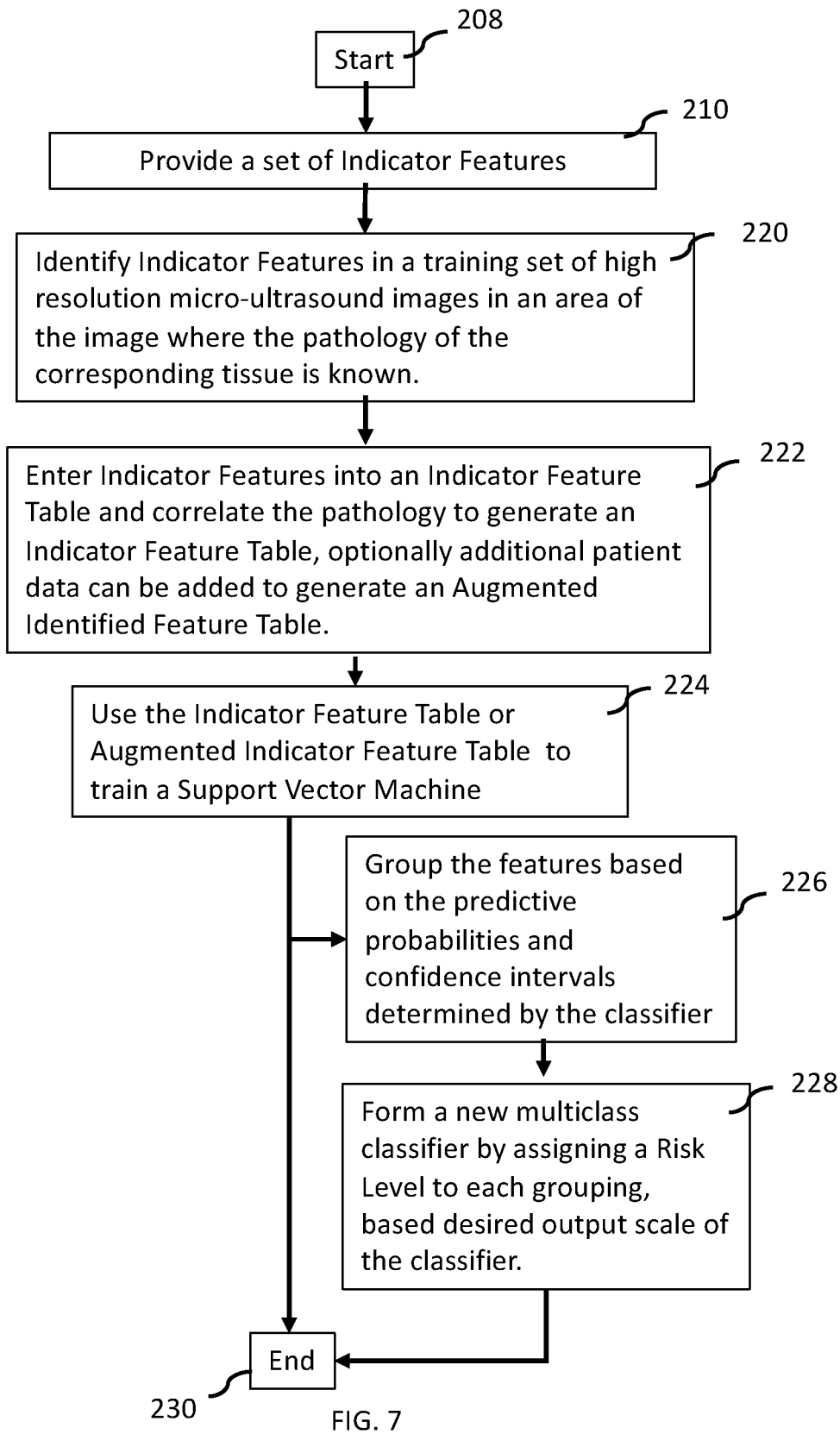
FIG. 7 is a flow diagram which illustrates a method for using Indicator Features to train a binary classification tree classifier and optionally a multiclass classifier in accordance with an embodiment of the invention.

Reference is now being made to the flow diagram of FIG. 7, which illustrates one embodiment of the present method for generating a classifier and/or multiclassifier comprising Indicator Features high resolution micro-ultrasound images. FIG. 7 illustrates the process of training a support vector machine using an Indicator Feature Table or Augmented Indicator Feature Table. Flow processing begins at step 208 and immediately proceeds to step 210. At step 210, provide a set of Indicator Features. At step 220, identify Indicator Features in each of the training images in an area of the image where the pathology is known, but blinded to the reader. At step 222, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 224, the Indicator Feature Table or the Augmented Feature Table is used to train a support vector machine. The process can stop here at step 230, or optionally, proceed to step 226, to group the features based on the predictive probabilities of each Indicator Feature and/or combination of Indicator Features. At step 228, form a new multiclass classifier based on the desired output scale of the classifier and the groupings of the features and the desired confidence intervals. Optionally, the classifier or the multiclass classifier can be further trained using either training data or test data.

Quadratic programming techniques such as Sequential Minimization Optimization or Iterative Single Data Algorithm may be applied to determine the N-dimensional hyperplane best separating the benign from cancerous data points (where N is the number of biopsy samples available, the number of rows in the feature matrix). A kernel function is not required so long as independent, binary feature values are used. Output "score" or posterior probability of cancer may be determined through the linear equation $f(x)=x'\beta+\beta 0$, where beta is the vector orthogonal to the classification hyperplane.

Artificial Neural Networks

Figure 8:
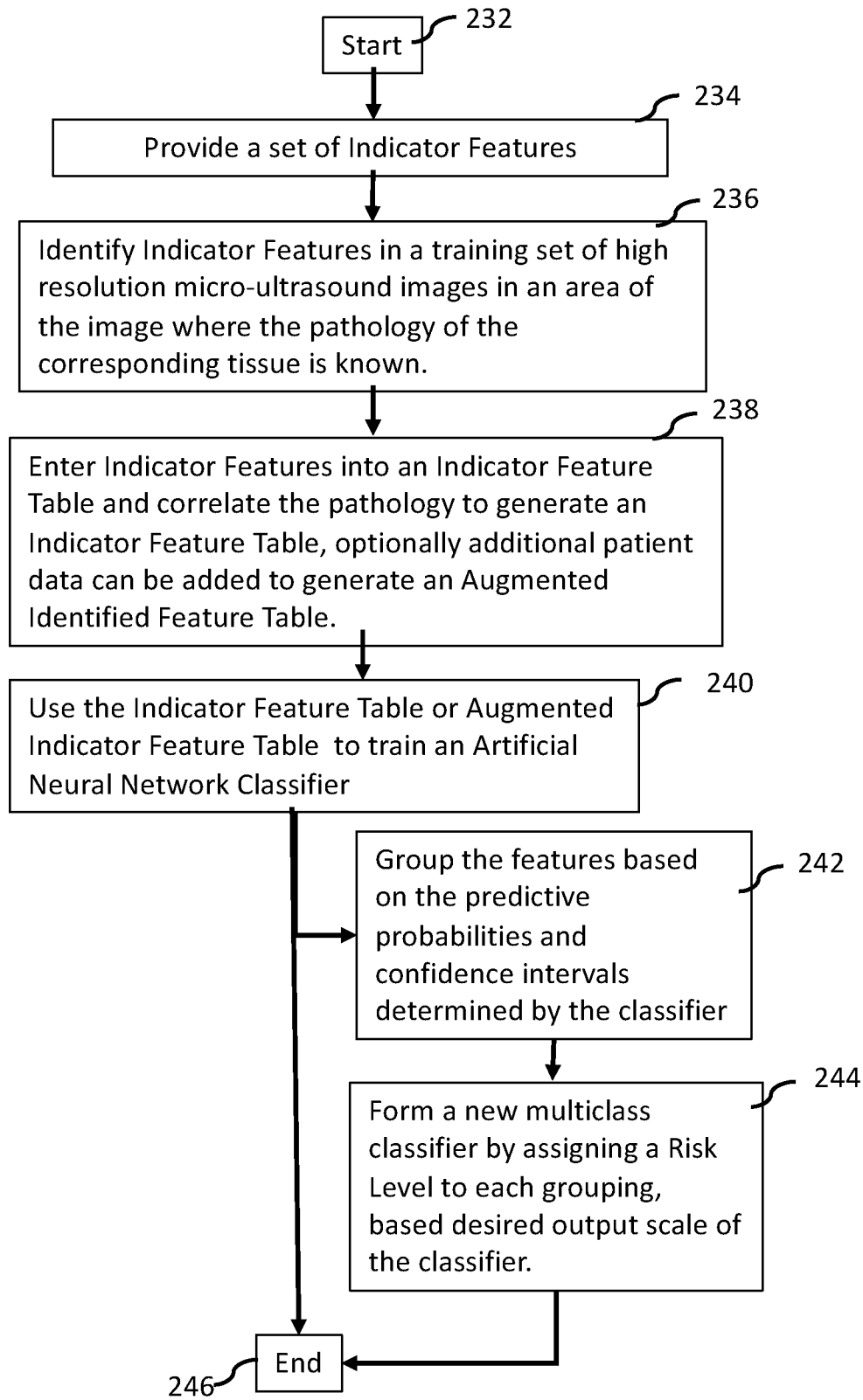
FIG. 8 is a flow diagram which illustrates a method for using Indicator Features to train an artificial neural network classifier and optionally a multiclass classifier in accordance with an embodiment of the invention.

Reference is now being made to the flow diagram of FIG. 8, which illustrates one embodiment of the present method for generating a classifier and/or multiclassifier comprising Indicator Features high resolution micro-ultrasound images. FIG. 8 illustrates the process of training an artificial neural network classifier using an Indicator Feature Table or Augmented Indicator Feature Table. Flow processing begins at step 232 and immediately proceeds to step 234. At step 234, provide a set of Indicator Features. At step 238, identify Indicator Features in each of the training images in an area of the image where the pathology is known, but blinded to the reader. At step 238, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 240, the Indicator Feature Table or the Augmented Feature Table is used to train an artificial neural network classifier. The process can stop here at step 246, or optionally, proceed to step 242, to group the features based on the predictive probabilities of each Indicator Feature and/or combination of Indicator Features. At step 244, form a new multiclass classifier based on the desired output scale of the classifier and the groupings of the features and the desired confidence intervals. Optionally, the classifier or the multiclass classifier can be further trained using either training data or test data.

An artificial neural network may be created with N input nodes (one for each feature) and a single output node with a continuous output representing the probability of cancer. In between these input and output nodes are M layers of perceptrons each summing weighted input from the previous layer and exhibiting a sigmoidal response curve. These weights are determined through a backpropagation algorithm, which is well described in the literature. Briefly:
1. Split the data into training and validation sets (for example 80%/20%, depending on size of data set).
2. For a given training example, and starting set of weights the response of each layer is calculated sequentially until the output is reached.
3. The error (i.e. mean squared error) between the output and truth is calculated and propagated backwards through the system layer-by-layer, modifying each weight by a portion of the gradient.
4. Calculate error in validation set.
5. Repeat from 2 for each training example, using the current set of weights until validation set error is no longer decreasing.

Naïve Bayesian Networks

Figure 9:
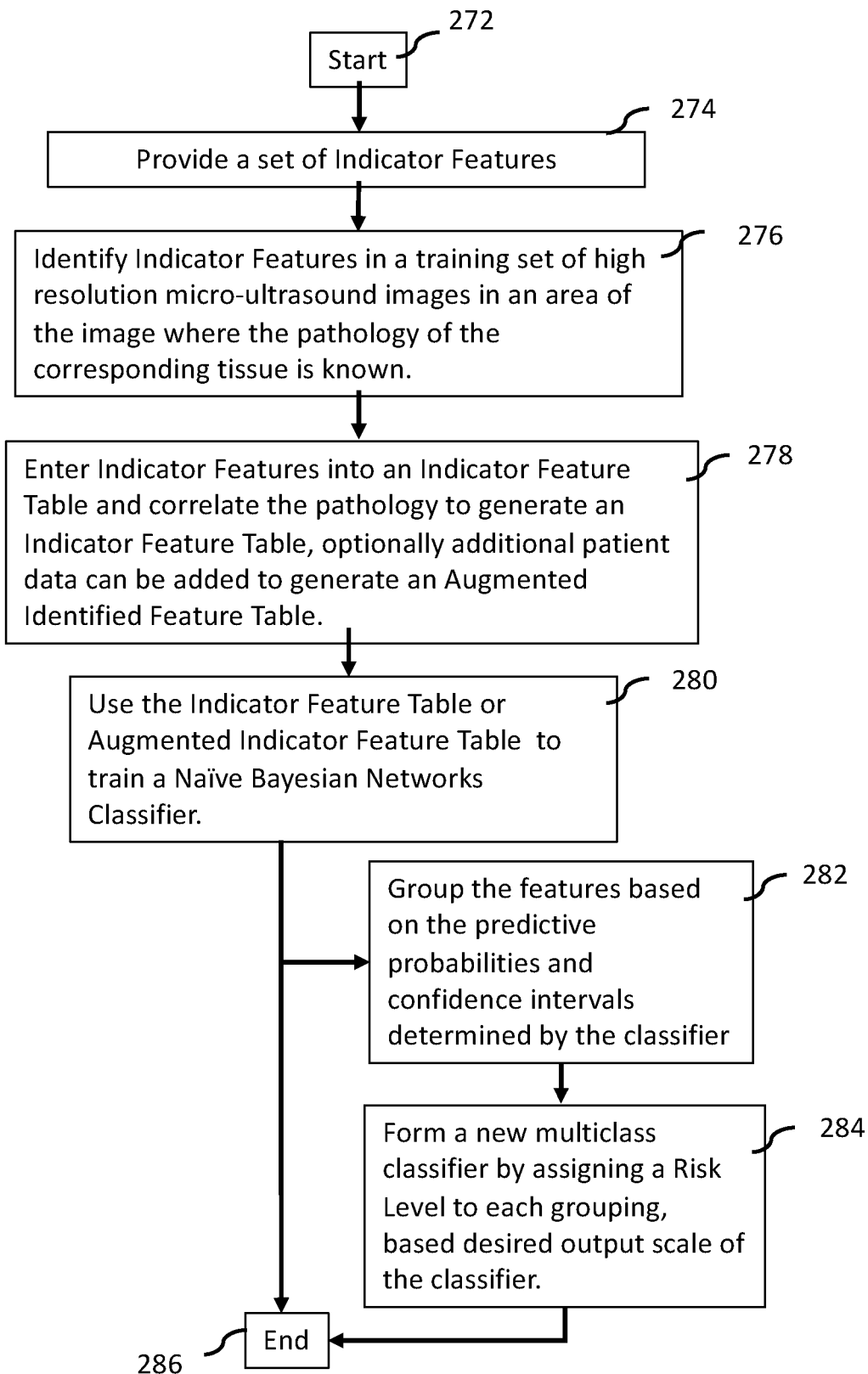
FIG. 9 is a flow diagram which illustrates a method for using Indicator Features to train a naïve Bayesian network classifier and optionally a multiclass classifier in accordance with an embodiment of the invention.

Reference is now being made to the flow diagram of FIG. 9, which illustrates one embodiment of the present method for generating a classifier and/or multiclassifier comprising Indicator Features high resolution micro-ultrasound images. FIG. 9 illustrates the process of training a naïve Bayesian network classifier using an Indicator Feature Table or Augmented Indicator Feature Table. Flow processing begins at step 272 and immediately proceeds to step 274. At step 274, provide a set of Indicator Features. At step 276, identify Indicator Features in each of the training images in an area of the image where the pathology is known, but blinded to the reader. At step 278, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 280, the Indicator Feature Table or the Augmented Feature Table is used to train an artificial neural network classifier. The process can stop here at step 286, or optionally, proceed to step 282, to group the features based on the predictive probabilities of each Indicator Feature and/or combination of Indicator Features. At step 284, form a new multiclass classifier based on the desired output scale of the classifier and the groupings of the features and the desired confidence intervals. Optionally, the classifier or the multiclass classifier can be further trained using either training data or test data.

Given the matrix of Boolean (Bernoulli) features, a naïve bayes classifier may be trained using:

$$\text{weight}_i = \ln \frac{\text{Occurance rate of feature } i \text{ in Cancerous Tissue}}{\text{Occurance rate of feature } i \text{ in Benign Tissue}}$$

And a new sample queried using:

$$\text{Score} = \ln \frac{\text{\# Cancers}}{\text{\# Benigns}} + \sum_i \text{weight}_i \cdot \text{Feature}_i$$

Where scores >0 are indicative of cancer. To avoid issues with numerical stability arising from a limited data set, a small positive value may be added to the numerator and denominator in each of the above ratios in order to ensure finite outputs.

Linear Discriminant Analysis

FIG. 8 illustrates the process of training a linear discriminate analysis classifier using an Indicator Feature Table or Augmented Indicator Feature Table.

Figure 10:
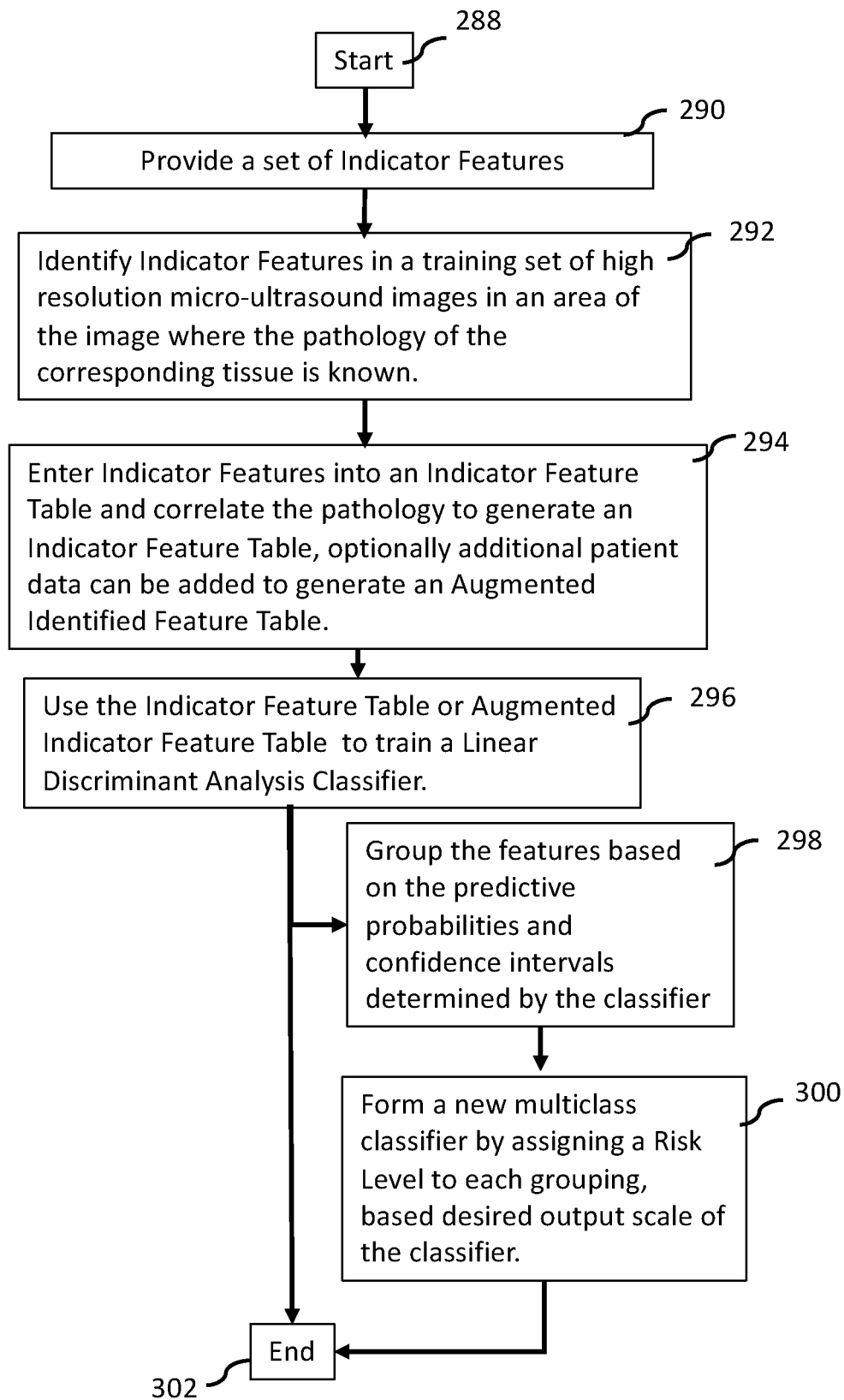
FIG. 10 is a flow diagram which illustrates a method for using Indicator Features to train a linear discriminant analysis classifier and optionally a multiclass classifier in accordance with an embodiment of the invention.

Reference is now being made to the flow diagram of FIG. 10, which illustrates one embodiment of the present method for generating a classifier and/or multiclassifier comprising Indicator Features high resolution micro-ultrasound images. FIG. 10 illustrates the process of training a linear discriminate analysis classifier using an Indicator Feature Table or Augmented Indicator Feature Table. Flow processing begins at step 288 and immediately proceeds to step 290. At step 290, provide a set of Indicator Features. At step 292, identify Indicator Features in each of the training images in an area of the image where the pathology is known, but blinded to the reader. At step 294, the pathology data is linked to the sonographic features in the Indicator Feature Table because the tissue sample and training image are taken from the same physical location in the prostate. Optionally, additional information can be added to the Indicator Feature Table to generate an Augmented Feature Table. At step 296, the Indicator Feature Table or the Augmented Feature Table is used to train a linear discriminate analysis classifier. The process can stop here at step 302, or optionally, proceed to step 298, to group the features based on the predictive probabilities of each Indicator Feature and/or combination of Indicator Features. At step 300, form a new multiclass classifier based on the desired output scale of the classifier and the groupings of the features and the desired confidence intervals. Optionally, the classifier or the multiclass classifier can be further trained using either training data or test data.

The threshold for classifying benign and cancerous tissue may be calculated using linear discriminant analysis, according to the following equations:

$$w = (\Sigma_B + \Sigma_C)^{-1}(\mu_C - \mu_B)$$

$$c = w^{1/2}(\mu_C + \mu_B)$$

Where all quantities are vectors in the N-dimensional feature space, $\mu$ are the class means, $\Sigma$ are the class covariances, and the subscripts B and C are for the benign and cancerous classes respectively. The vector w then represents the normal to the hyperplane separating the two classes and scalar c the threshold along that hyperplane. A new observation (N) may be classified by multiplying by w and then finding the distance (i.e. $\|c-wN\|$) and sign (i.e. $\text{sgn}(c-wN)$) to the point c.

Validating the Classifier

Methods of validating a classifier are well known to one skilled in the art. In general, a classifier is validated by using it with a new independent set of images for which the pathology is known (including a mixture of both benign and malignant tissue) but not revealed to the person or computer reading the images to determine the presence of Indicator Features. The results are entered into an Indicator Feature Table and correlated with the pathology. This data is used to calculate ROC's for each reader. Accuracy is calculated by using the AUC under each reader's ROC.

Exemplary Results

Here are presented some preliminary results of a method according to an embodiment of the invention. FIG. 11 shows exemplary sonographic features used in an embodiment of a multiclass classifier.

FIG. 11A: Biopsy-proven benign tissue showing ductal proliferation. This regular ductal pattern was labeled as "swiss cheese" appearance.

FIG. 11B: Biopsy-proven benign tissue showing hyperechoic and ductal regions. The presence or absence of these scattered ducts was not found to significantly affect risk level.

FIG. 11C: This tissue was found to be benign on biopsy despite the mild hypoechoic region on the right. The tissue exhibits mild heterogeneity and includes small bright echos (focal bright points within the tissue) in otherwise hyperechoic tissue.

FIGS. 11D, 11E, and 11F These images show higher risk patterns, from left to right:

11D: Strong bright echos in hypoechoic tissue (GS8);

11E: Heterogenous "smudgy" or "mottled" tissue (GS7), and

11F: Heterogenous "Cauliflower" or

Focal Nodular Hyperplasia type tissue (GS8).

All three biopsy samples were found to be malignant with Gleason Sums of 8, 7, and 8 respectively.

FIG. 11G: Irregular shadowing presents as vertical hypoechoic regions with no obvious source of attenuation (such as a calcification or gas bubble). FIG. 11H: a mixed echo lesion with well-defined borders is present pressing on the rectal wall causing the prostate border to be irregular. In both cases the biopsy samples show a Gleason Sum of 9.

A Database of High Resolution Prostate Images

A database comprising high resolution micro-ultrasound prostate images, wherein Indicator Features in the images have been correlated to tissue biopsy results and optionally a risk score assigned by a classifier or multiclass classifier. The database is structured to: i) permit queries regarding co-occurrence of features, ii) examine various instances of each feature in order to train an automated analysis system such as a deep learning image analyzer to recognize the features; and iii) add new images, marked with indicator features so that the method can be continually improved by providing a better assessment of the predicted probability of cancer for each feature or combination of features.

The database can optionally comprise additional data pertaining to the patient data obtained from, B-mode (greyscale) images, Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

FIG. 14 is a block diagram of an exemplary computer system for implementing a method and system for classifying a patient's risk of having prostate cancer according to an embodiment of the invention. Referring now to FIG. 14, a computer system 700 for implementing the present invention can comprise, inter alia, a central processing unit (CPU) 702, a memory 704 and an input/output (I/O) interface 706. The computer system 700 is generally coupled through the I/O interface 706 to a display 708 and various input devices 710 such as a mouse and a keyboard. The support circuits can include circuits such as cache, power supplies, clock circuits, and a communication bus. The memory 704 can include random access memory (RAM), read only memory (ROM), disk drive, tape drive, etc., or a combinations thereof. The present invention can be implemented as a routine 712 that is stored in memory 704 and executed by the CPU 702 to process the signal from the signal source 714. As such, the computer system is a general purpose computer system that becomes a specific purpose computer system when executing the routine 712 of the present invention.

The computer system 700 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

Flow Diagram of One Embodiment of Using the Classifier

Reference is now being made to the flow diagram of FIG. 16 which illustrates one embodiment of the present method using the multiclass classifier for classifying patient risk for prostate cancer in accordance with the teachings hereof. Flow processing begins at step 400 and immediately proceeds to step 402.

At step 402, receive a database of micro-ultrasound images containing Indicator Features and correlated to pathology results. At step 404, use the system/method described above to train a classifier system or multi class classifier system, which functions to classify an unclassified patient into one of a plurality of risk levels. At step 406, obtain the sonogram of a patient to be classified, and read the image for the presence of any of the features indicated by the classifier or multiclass classifier of 404. This step may occur in real time during the biopsy procedure with a "live" image, or post hoc based on a saved image. In one embodiment, the features are: Small regular ducts, Hyperechoic tissue with our without ductal patches, mild heterogeneity, bright echoes in hyperechoic tissue, heterogeneous appearance, bright echoes, irregular peripheral zone, irregular prostate border, mixed-echo lesions, irregular shadowing.

At step 408, if a multiclass classifier is selected, use the multiclass classifier to classify the unclassified image into one of a plurality of classes. In an embodiment, this is accomplished by the operator consulting a printed flow chart or other visual aid (for example, see FIG. 12) generated based on step 404 which begins with high-risk features and proceeds to low risk features. In another embodiment, an automated system is used to classify the image.

Reference is now being made to the flow diagram of FIG. 17 which is a continuation of the flow diagram of FIG. 16 with flow processing continuing with respect to Node B. At step 412, communicate the image's classification to a display device. In other embodiments, the patient classification is communicated to any of: a storage device, a wireless handheld device, a laptop, tablet-PC, and a workstation. At step 414, a determination is made whether the classified image suggests a significant risk for having prostate cancer.

At step 416, if the operator is conducting a live prostate biopsy, and the portion of tissue identified by the image in step 414 is determined to suggest a significant or elevated risk of prostate cancer, a targeted biopsy may be taken to confirm the diagnosis. Similarly, if images are being analyzed off-line in an active surveillance patient and the tissue identified by the image in step 414 is determined to have increased in risk level, the patient may be recalled so that a new biopsy sample may be taken, or potentially recommended for treatment.

At step 420, a determination is made whether to perform another classification. If so then processing repeats with respect to node D wherein, at step 408, more images are obtained from this same patient. Processing repeats in a similar manner. If it is determined that further patient classification is not to be performed then, in this embodiment, further processing stops.

At step 418, once pathology results have been gathered (e.g., step 417) for any biopsy or radical prostatectomy samples taken, the identified sonographic features and corresponding pathology may optionally be added (step 418) to the database of step 402. Step 404 may then be repeated to improve the classification system. It should be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Reference is now being made to FIG. 18 which shows a block diagram of one example system for performing various aspects of the present (using the Classifier)

In FIG. 18, a training set (collectively at 501) comprising images for a plurality of subjects are retrieved from a database 502. Database 502 is a storage device wherein records are stored, manipulated, and retrieved in response to a query. Such records, in various embodiments, take the form of Tables of Indicator Features and/or Tables of Augmented Indicator Features. Although the database is shown as an external device, the database 502 may be internal to the workstation mounted, for example, on a hard disk therein. The training set is provided to the classifier system for training purposes. The features of the training set are obtained from the sonographic images In the embodiment shown, the classifier system comprises a plurality of modules. Learning Module 503 processes the training data contained in the records of the training set such that the classifier system can be trained. The Learning Module 503 further functions to prune the training set, as desired, such that the classifier is trained with data which meet a pre-determined criteria such as acceptable image quality. Once training has completed, Learning Module 503 signals Classification Module 504 to receive an image of a yet-to-be classified patient 506. The unclassified patient's images 506 are received or are otherwise obtained by the classifier system which, in turn, proceeds to classify the unclassified image into one of a number of risk levels.

Processor retrieves machine readable program instructions from Memory 505 and is provided to facilitate the functionality of the various modules comprising the classifier system. The processor, operating alone or in conjunction with other processors and memory, may be configured to assist or otherwise facilitate the functionality of any of the processors and modules of system.

The classifier system of FIG. 18 is shown in communication with a workstation. A computer case of the workstation houses various components such as a motherboard with a processor and memory, a network card, a video card, a hard drive capable of reading/writing to machine readable media such as a floppy disk, optical disk, CD-ROM, DVD, magnetic tape, and the like, and other software and hardware needed to perform the functionality of a computer workstation. The workstation further includes a display device, such as a CRT, LCD, or touchscreen device, for displaying information, video, measurement data, computed values, medical information, results, locations, and the like. A user can view any of that information and make a selection from menu options displayed thereon. Keyboard and mouse effectuate a user input.

It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation is further enabled to display the sonographic image and patient classifications as they are derived. The workstation may further display interim values, boundary conditions, and the like, in real-time as the classifier system performs its intended functionality as described herein in detail.

A user or technician may use the user interface of the workstation to set parameters, view/adjust/delete values in the training set, and adjust various aspects of the classifier system as needed or as desired, depending on the implementation. Any of these selections or input may be stored/retrieved to storage device. Default settings can be retrieved from the storage device. A user of the workstation is also able to view or manipulate any of the records contained in the training set via pathways not shown.

Although shown as a desktop computer, it should be appreciated that the workstation can be a laptop, mainframe, or a special purpose computer such as an ASIC, circuit, or the like. The embodiment of the workstation of FIG. 18 is illustrative and may include other functionality known in the arts. Any of the components of the workstation may be placed in communication with the classifier system or any devices in communication therewith. Any of the modules of the classifier system can be placed in communication with storage device and/or computer readable media and may store/retrieve therefrom data, variables, records, parameters, functions, and/or machine readable/executable program instructions, as needed to perform their intended functions. Each of the modules of the classifier system may be placed in communication with one or more remote devices over network.

It should be appreciated that some or all of the functionality performed by any of the modules or processing units of the video processing system can be performed, in whole or in part, by the workstation placed in communication with the classifier system over network. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service.

The following clauses are offered as further description of the examples of the apparatus. Any one or more of the following clauses may be combinable with any another one or more of the following clauses and/or with any subsection or a portion or portions of any other clause and/or combination and permutation of clauses. Any one of the following clauses may stand on its own merit without having to be combined with any other clause or any portion of any other clause, etc. CLAUSE 1: A method of any clause in this paragraph, for generating one or more Indicator Features in high resolution ultrasound images, which can be used in assigning risk of prostate cancer during high resolution micro-ultrasound imaging the method comprising the steps of: i) generating a list of Possible Features in the images by: a) obtaining a high resolution micro-ultrasound image of prostate tissue that corresponds to tissue, which has also been biopsied and has been graded for a stage of cancer, ranging from benign to the highest grade; b) segmenting the region of the image corresponding to the biopsied tissue on the basis of contrasting areas or groups of pixels in the image, wherein each area or group of pixels constitutes a feature; and c) characterizing and providing a unique label to all detectable features and/or combination of features only in the region of the image that corresponds to biopsied tissue, ii) repeat steps a) through d) until all recurring patterns have been included in the list of Possible Features; iii) generate a Table of Candidate Features by: d) reading the micro-ultrasound images in the area corresponding to tissue, which has been graded for a stage of cancer, but for which the results are not known to the reader, identify and record in the Table the Candidate Features and/or combinations of Candidate Features observed in the area corresponding to graded tissue; e) correlating in the Table of Candidate Features the stage of cancer in the biopsied tissue that corresponds to the area in the image where each of the Candidate Features and/or combinations of Candidate Features are identified, wherein the stage ranges from benign to the highest grade; f) use the Table of Candidate Features as a training set of features to train a linear or nonlinear classifier to classify an Candidate Feature or combination of Candidate Features as cancerous or non-cancerous and thereby determine a predicted probability of cancer for a given Candidate Feature or combination of Candidate Features; g) eliminate Candidate Features or combinations of Candidate Features that do not yield predicted probabilities required for an Indicator Feature. CLAUSE 2: A method of any clause in this paragraph, wherein the areas are identified by analyzing groups of pixels. CLAUSE 3: A method of any clause in this paragraph, wherein the high resolution micro-ultrasound image is generated using an ultrasonic scanning device that can supply ultrasound at a center frequency of at least 15 MHz to 70 MHz. CLAUSE 4: A method of any clause in this paragraph, wherein the high resolution micro-ultrasound image is generated using an ultrasonic scanning device that can supply ultrasound at a center frequency of about 22 MHz. CLAUSE 5: A method of any clause in this paragraph, wherein the image is: B-mode (grey-scale), Velocity Color Flow Imaging, Power Doppler Color Flow Imaging, Elastography, Contrast Enhancement, and/or Spectral Analysis. CLAUSE 6: A method of any clause in this paragraph, wherein the biopsied tissue is obtained by: i) needle biopsy; ii) partial prostatectomy; iii) radical prostatectomy; or iv) a sample taken during focal therapy. CLAUSE 7: A method of any clause in this paragraph, wherein the reading is conducted by: i) a human; ii) a machine (computer/computing machine?—optics plus computer); or iii) a human and a machine. CLAUSE 8: A method of any clause in this paragraph, wherein one or more Indicator Features obtained by the method of clause 7. CLAUSE 9: A method of any clause in this paragraph, wherein additional patient data is incorporated in the Table of Candidate Features and correlated with each Candidate Feature or combination of Candidate Features to the stage of cancer present in the tissue to generate an Augmented Table of Candidate Features, which is then used to train a non-linear classifier at step f). CLAUSE 10: A method of any clause in this paragraph, wherein the additional patient data comprises obtained from: spatial information about the image, spatial information about the features, 3-D information, spectral information about the image, and, images collected using other modalities such as B-mode (grey-scale), Velocity Color Flow Imaging, Power Doppler Color Flow Imaging, Elastography, Contrast Enhanced Ultrasound, Spectral Analysis, conventional resolution ultrasound, MRI, CT, or PET imaging, patient age, DRE results, PSA readings, free PSA, PSA density, family history, race, prostate volume, transition zone volume, relevant biomarkers, protein/hormonal biomarker levels, genetic screening results, or number of prior negative biopsies. CLAUSE 11: A method of any clause in this paragraph, one or more Indicator Features obtained by the method of clause 10. CLAUSE 12: A method of any clause in this paragraph, including additional steps for generating a classifier, the method comprising the steps of: i) providing a Training Set of Indicator Features comprising Indicator Features and/or combinations of Indicator Features correlated to pathology of the tissue; ii) using the Training Set of Indicator Features to train a linear or nonlinear classifier that classifies a Indicator Features and/or combinations of Indicator Features as benign or cancerous and thereby determine a predicted probability of cancer for an Indicator Feature and/or combinations of Indicator Features. CLAUSE 13: A method of any clause in this paragraph, comprising the additional step of constructing a Risk Table comprising features and/or combinations of features correlated to their predicted probability. CLAUSE 14: A method of any clause in this paragraph, further comprising a Risk Table generated following the method of CLAUSE 13. CLAUSE 15: A method of any clause in this paragraph, wherein the linear classifier is: univariate relative risk, linear discriminate analyzer, or a naïve Bayesian classifier. CLAUSE 16: A method of any clause in this paragraph, wherein the linear classifier calculates a univariate relative risk (RR) and a confidence interval (CI) are calculated for each Indicator Feature and/or combination of Indicator Features. CLAUSE 17: A method of any clause in this paragraph, wherein the non-linear classifier is a: binary classification tree, "random forest", support vector machine, or artificial neural network. CLAUSE 18: A method of any clause in this paragraph, wherein the classifier is executed by a computer comprising the steps of a patient image being read by the computer and processed to generate a predicted probability that the image relates to tissue that is cancerous. CLAUSE 19: A method of any clause in this paragraph, additionally comprising the step of including additional patient data into the Training Set of Indicator Features, wherein the additional risk parameters are correlated to an Indicator Feature or combination of Indicator Features. CLAUSE 20: A method of any clause in this paragraph, wherein the additional patient data comprises data obtained from: B-mode (grey-scale), Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies. CLAUSE 21: A method of any clause in this paragraph, wherein the results of a high resolution micro-ultrasound image that has been classified using the classifier are combined into a risk table with additional data pertaining to the patient based on data obtained from: B-mode (grey-scale) images, Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies. CLAUSE 22: A method of any clause in this paragraph, wherein additional patient data is added to the risk table to generate an Augmented Table, which is then used to train a linear or non-linear classifier. CLAUSE 23: A method of any clause in this paragraph, additionally comprising steps to construct a multiclass classifier, wherein the additional steps are: (i) grouping the Indicator Features and combinations of Indicator Features based on the predicted probabilities and confidence intervals determined by the classifier; and (ii) forming a new multiclass classifier by assigning a risk level to each grouping of Indicator Features, based on the desired output scale of the classifier. CLAUSE 24: A method of any clause in this paragraph, wherein the Indicator Features and/or combinations of Indicator Features are grouped based on the relative risk and confidence interval of each the Indicator Features and/or combinations of Indicator Features. CLAUSE 25: A method of any clause in this paragraph, wherein predefined thresholds are used to group features based on mean relative risk values. CLAUSE 26: A method of any clause in this paragraph, wherein a data set comprising balanced numbers of cancerous and benign observations, these predetermined values split the theoretical 0-2 range of the relative risk value into sections that provide useful assessment of the underlying risk. CLAUSE 27: A method of any clause in this paragraph, wherein the indicator features are assigned a risk level in the output scale based on their relative risk (RR) value according to the following categories: i) a mean RR range of 0.0-0.4 is assigned to be a very low risk; ii) a mean RR range of 0.4-0.6 is assigned to be some risk; iii) a mean RR range of 0.6-1.2 is assigned to be indeterminate risk; iv) a mean RR range of 1.2-1.6 is assigned to be significant risk; and v) a mean RR range of 1.6+ is assigned to be very high risk. CLAUSE 28: A method of any clause in this paragraph, wherein automated thresholding is used to determine the output scale. CLAUSE 29: A method of any clause in this paragraph, wherein the automated thresholding procedure comprises: i) choosing the pair of values with closest mean RR and comparing their CI ranges; ii) determining if the CI ranges overlap by a certain percentage, and if so, combining the values; iii) assigning the new mean for the group as the mean of the component RR values, and the CI as the intersection of the individual CI ranges; iv) repeat steps i) through iii) until no further merges are possible; v) repeat steps i) through iv) for the pair of values with the next closest mean RR values: vi) repeat steps i) through v) until every pair has been checked without a merge; viii) the resulting groups are sorted by their mean RR values and assigned Risk Scores from 1 (lowest RR) to N (highest RR). The overlap percentage may be adjusted to give a desirable number of classes for training purposes. CLAUSE 30: A method of any clause in this paragraph, wherein k-nearest neighbors clustering may be used with a fixed number of predefined starting classes spaced evenly over the RR space. CLAUSE 31: A method of any clause in this paragraph, wherein the multiclass classifier has between 3-10 possible risk levels. CLAUSE 32: A method of any clause in this paragraph, wherein the multiclass classifier comprises 5 possible risk levels of: a) very low risk for small regular ducts "Swiss cheese" with no other heterogeneity or bright echoes; b) some risk for hyperechoic, with or without ductal patches (possible ectatic glands or cysts); c) indeterminate risk for mild heterogeneity or bright echoes in hyperechoic tissue; d) significant risk for heterogeneous "cauliflower/smudgy/mottled" appearance or bright echoes; and e) very high risk for irregular shadowing originating within the prostate, not the prostate border, or mixed-echo lesions or irregular prostate and/or PZ border. CLAUSE 33: A method of any clause in this paragraph, a multiclass classifier generated according to the method of clause 32. CLAUSE 34: A method of any clause in this paragraph, wherein the multiclass classifier comprises 5 possible risk levels of: a) very low risk for small regular ducts or "Swiss Cheese" feature; b) some risk for hyperchoic with/without ductal patches features; c) indeterminate risk for a mild heterogeneity or bright echoes in hyperechoic tissue; d) significant risk for heterogeneous "cauliflower, smudgy or mottled" or bright echoes "starry sky" features; and e) very high risk for irregular shadowing or mixed-echo lesions or irregular prostrate/PZ border. CLAUSE 35: A method of any clause in this paragraph, a multiclass classifier generated according to the method of clause 34. CLAUSE 36: A method of any clause in this paragraph, the method of using the multiclass classifier of clause 32 to assist in the diagnosis of prostate cancer. CLAUSE 37: A method of any clause in this paragraph, the method of using the multiclass classifier of clause 35 to assist in the diagnosis of prostate cancer. CLAUSE 38: A method of any clause in this paragraph, the method of using the multiclass classifier of clause 32 to direct a clinician as to where to take a biopsy core from the prostate. CLAUSE 39: A method of any clause in this paragraph, the method of using the multiclass classifier of clause 35 to direct a clinician as to where to take a biopsy core from the prostate. CLAUSE 40: A method of any clause in this paragraph, a plurality of Indicator Features generated according to the method of clause 7, comprising the same or similar characteristics as: a) small regular ducts "Swiss cheese"; b) hyperechoic with or without ductal patches; c) mild heterogeneity; d) bright echoes in hyperechoic tissue; e) heterogeneous "cauliflower/smudgy/ mottled" appearance; f) bright echoes; g) irregular prostate (PZ); h) irregular prostate border; i) mixed-echo lesions; or j) irregular shadowing. CLAUSE 41: A method of any clause in this paragraph, a plurality of Indicator Features generated according to the method of clause 7, comprising the same or similar characteristics as: a) regular ductal pattern "Swiss cheese"; b) hyperechoic with ductal patches; c) mild heterogeneity with small bright echoes in hyperchoic tissue; d) bright echoes; e) heterogeneous "smudged/mottled"; f) heterogeneous "cauliflower"; g) irregular shadowing; or h) mixed echo lesion causing irregular prostate borders. CLAUSE 42: A method of any clause in this paragraph, one or more Indicator Features having the same or similar characteristics as: i) small regular ducts "Swiss cheese"; ii) regular ductal pattern "Swiss cheese"; iii) hyperechoic with ductal patches; iv) hyperechoic with or without ductal patches; v) mild heterogeneity with small bright echoes in hyperechoic tissue; vi) mild heterogeneity; vii) bright echoes in hyperechoic tissue; viii) heterogeneous "smudged/ mottled"; ix) heterogeneous "cauliflower"; x) heterogeneous "cauliflower/smudgy/mottled" appearance; xi) bright echoes; xii) irregular prostate (PZ); xiii) irregular prostate border; xiv) mixed-echo lesions; xv) irregular shadowing; or xvi) mixed echo lesion causing irregular prostate borders. CLAUSE 43: A method of any clause in this paragraph, a method for generating a classifier, the method comprising the steps of: i) providing a Training Set of Indicator Features in high resolution micro-ultrasound images of prostate comprising Indicator Features and/or combinations of Indicator Features correlated to pathology of the tissue; ii) using the Training Set of Indicator Features to train a linear or nonlinear classifier that classifies a Indicator Features and/or combinations of Indicator Features as benign or cancerous and thereby determine a predicted probability of cancer for an Indicator Feature and/or combinations of Indicator Features. CLAUSE 44: A method of any clause in this paragraph, a classifier generated according to the method of clause 43. CLAUSE 45: A method of any clause in this paragraph, additionally comprising steps to construct a multiclass classifier, wherein the additional steps are: grouping the Indicator Features and combinations of Indicator Features based on the predicted probabilities and confidence intervals determined by the classifier; and forming a new multiclass classifier by assigning a risk level to each grouping of Indicator Features, based on the desired output scale of the classifier. CLAUSE 46: A method of any clause in this paragraph, a multiclass classifier generated according to the method of clause 45. CLAUSE 47: A program storage device of any clause in this paragraph, the program storage device readable by a computer tangibly embodying a program of instructions executable by the computer to perform the method steps for generating Indicator Features in high resolution micro-ultrasound prostate images, the method comprising the steps of: i) generating a list of Possible Features in the images by: a. obtaining a high resolution micro-ultrasound image of prostate tissue that corresponds to tissue, which has also been biopsied and has been graded for a stage of cancer, ranging from benign to the highest grade; b. segmenting the region of the image corresponding to the biopsied tissue on the basis of contrasting areas in the image, wherein each area constitutes a feature; and c. characterizing and providing a unique label to all detectable features and/or combination of features only in the region of the image that corresponds to biopsied tissue, ii) repeat steps a) through c) until all recurring patterns have been included in the list of Possible Features; iii) generate a Table of Candidate Features by: a) obtaining a training set of new high resolution micro-ultrasound image of prostate tissue that corresponds to tissue, which has also been subsequently biopsied and has been graded for a stage of cancer, ranging from benign to the highest grades; b) reading the micro-ultrasound images in the area corresponding to tissue, which has been graded for a stage of cancer, but for which the results are not known to the reader, identify and record in the Table the Candidate Features and/or combinations of Candidate Features observed in the area corresponding to graded tissue; c) correlating in the Table of Candidate Features the stage of cancer in the biopsied tissue that corresponds to the area in the image where each of the Candidate Features and/or combinations of Candidate Features are identified, wherein the stage ranges from benign to the highest grade; d) use the Table of Candidate Features as a training set of features to train a linear or nonlinear classifier to classify an Candidate Feature or combination of Candidate Features as cancerous or non-cancerous and thereby determine a predicted probability of cancer for a given Candidate Feature or combination of Candidate Features; e) eliminate Candidate Features or combinations of Candidate Features that do not yield predicted probabilities required for an Indicator Feature. CLAUSE 48: A program storage device of any clause in this paragraph, wherein the areas are identified by analyzing groups of pixels. CLAUSE 49: A program storage device of any clause in this paragraph, wherein the high resolution micro-ultrasound image is generated using an ultrasonic scanning device that can supply ultrasound at a center frequency of at least 15 MHz to 70 MHz. CLAUSE 50: A program storage device of any clause in this paragraph, wherein the high resolution micro-ultrasound image is generated using an ultrasonic scanning device that can supply ultrasound at a center frequency of about 22 MHz. CLAUSE 51: A program storage device of any clause in this paragraph, wherein the image is: B-mode (grey-scale), Velocity Color Flow Imaging, Power Doppler Color Flow Imaging, Elastography, Contrast Enhancement, and/or Spectral Analysis. CLAUSE 52: A program storage device of any clause in this paragraph, the program storage device readable by a computer tangibly embodying a program of instructions executable by the computer to perform the method steps for generating a classifier, the method comprising the steps of: i) providing a Training Set of Indicator Features in high resolution micro-ultrasound images of prostate comprising Indicator Features and/or combinations of Indicator Features correlated to pathology of the tissue; ii) using the Training Set of Indicator Features to train a linear or nonlinear classifier that classifies a Indicator Features and/or combinations of Indicator Features as benign or cancerous and thereby determine a predicted probability of cancer for an Indicator Feature and/or combinations of Indicator Features. CLAUSE 53: A program storage device of any clause in this paragraph, configured to perform the additional method steps to construct a multiclass classifier, wherein the additional steps are: i) grouping the Indicator Features and combinations of Indicator Features based on the predicted probabilities and confidence intervals determined by the classifier; and ii) forming a new multiclass classifier by assigning a risk level to each grouping of Indicator Features, based on the desired output scale of the classifier. CLAUSE 54: A database of any clause in this paragraph, the database comprising high resolution micro-ultrasound prostate images, wherein Indicator Features in the images have been correlated to tissue biopsy results and optionally a risk score assigned by a classifier or multiclass classifier, wherein the database is structured to: i) permit queries regarding co-occurrence of features, and ii) examine various instances of each feature in order to train an automated analysis system such as a deep learning image analyzer to recognize the features iii) add new images, marked with indicator features so that the method can be continually improved by providing a better assessment of the predicted probability of cancer for each feature or combination of features. CLAUSE 55 A database of any clause in this paragraph, comprising additional data pertaining to the patient based on data obtained from: B-mode (grey-scale) images, Velocity Color Flow Imaging, Power Doppler Color Flow Imaging, Elastography, Contrast Enhanced Ultrasound, Spectral Analysis, conventional resolution ultrasound, MRI, CT, or PET imaging, patient data comprising patient age, DRE results, PSA readings, free PSA, PSA density, family history, race, prostate volume, transition zone volume, relevant biomarker levels, protein/hormonal biomarker levels, genetic screening results, or number of prior negative biopsies.

It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The teachings of any publications referenced herein are each hereby incorporated by reference in their entirety.

While the present invention has been described in detail with reference to a preferred embodiment, those skilled in the art will appreciate that various modifications and substitutions can be made thereto without departing from the spirit and scope of the invention as set forth in the appended claims.

The invention claimed is:

1. A method for generating one or more Indicator Features in high resolution ultrasound images, which can be used in assigning risk of prostate cancer during high resolution micro-ultrasound imaging the method comprising the steps of:
   i) generating a list of Possible Features in the images by:
      a) obtaining a high resolution micro-ultrasound image of prostate tissue and surrounding tissue that contains biopsied prostate tissue, the biopsied prostate tissue having also been biopsied and graded for a stage of cancer, ranging from benign to the highest grade;
      b) segmenting a region of the image corresponding to the biopsied prostate tissue on the basis of contrasting areas or groups of pixels in the image, wherein each area or group of pixels constitutes a detectable feature; and
      c) characterizing and providing a unique label to all detectable features and/or combinations of detectable features only in the region of the image that corresponds to biopsied prostate tissue, the detectable features and/or combinations of detectable features with the unique labels comprising the list of Possible Features;
   ii) repeating steps a) through c) until all detectable recurring patterns have been included in the list of Possible Features;
   iii) generating a Table of Candidate Features by:
      d) reading the micro-ultrasound images in an area corresponding to graded prostate tissue which has been graded for a stage of cancer but for which a result for the stage of cancers is not known to a reader so as to identify Candidate Features and/or combinations of Candidate Features, wherein the Candidate Features and/or combinations of Candidate Features are a subset of the list of Possible Features;
      e) recording in the Table of Candidate Features the Candidate Features and/or combinations of Candidate Features observed in the area corresponding to graded prostate tissue;
   iv) eliminating non-predictive features from the Table of Candidate Features by:
      f) performing at least one of:
         1) correlating in the Table of Candidate Features the stage of cancer in the biopsied prostate tissue that corresponds to the area in the image where each of the Candidate Features and/or combinations of Candidate Features are identified, wherein the stage ranges from benign to the highest grade, wherein the correlation is a predicted probability of cancer for a given Candidate Feature or combination of Candidate Features; and
         2) using the Table of Candidate Features as a training set of features to train a linear or nonlinear feature elimination classifier to classify a Candidate Feature or combination of Candidate Features as cancerous or non-cancerous and thereby determining a predicted probability of cancer for a given Candidate Feature or combination of Candidate Features; and
      g) eliminating, from the Table of Candidate Features for generating the Indicator Features, Candidate Features or combinations of Candidate Features that have a predicted probability of cancer that is below a threshold value, the predicted probability of cancer being determined in step f).

2. The method of claim 1, wherein the high resolution micro-ultrasound image is generated using an ultrasonic scanning device that can supply ultrasound at a center frequency of 15 MHz to 70 MHz.

3. The method of claim 1, wherein the image is any one or a combination of: B-mode (grey-scale), Velocity Color Flow Imaging, Power Doppler Color Flow Imaging, Elastography, Contrast Enhancement, or Spectral Analysis.

4. The method of claim 1, wherein the reading is conducted by:
   i) a human;
   ii) a computer; or
   iii) a human and a computer.

5. The method of claim 1 wherein the one or more generated Indicator Features comprise:
   i) small regular ducts "Swiss cheese;"
   ii) regular ductal pattern "Swiss cheese";
   iii) hyperechoic with ductal patches;
   iv) hyperechoic with or without ductal patches;
   v) mild heterogeneity with small bright echoes in hyperechoic tissue;
   vi) mild heterogeneity;
   vii) bright echoes in hyperechoic tissue;
   viii) heterogeneous "smudged/mottled";
   ix) heterogeneous "cauliflower";
   x) heterogeneous "cauliflower/smudgy/mottled" appearance;
   xi) bright echoes;
   xii) irregular prostate (PZ);
   xiii) irregular prostate border;
   xiv) mixed-echo lesions;
   xv) irregular shadowing; or
   xvi) mixed echo lesion causing irregular prostate borders.

6. The method of claim 1, wherein additional patient data is incorporated in the Table of Candidate Features and correlated with each Candidate Feature or combination of Candidate Features to the stage of cancer present in the tissue to generate an Augmented Table of Candidate Features, which is then used to train a linear or non-linear classifier at step f).

7. The method of claim 1, including additional steps for training a classifier, the method comprising the steps of:
   i) providing a Training Set of Indicator Features comprising the Indicator Features and/or combinations of the Indicator Features correlated to pathology of the tissue;
   ii) using the Training Set of Indicator Features to train a linear or nonlinear classifier that classifies Indicator Features and/or combinations of Indicator Features as benign or cancerous and thereby determine a predicted probability of cancer for an Indicator Feature and/or combinations of Indicator Features.

8. The method of claim 7, additionally comprising the step of including additional patient data into the Training Set of Indicator Features, wherein the additional patient data is correlated to an Indicator Feature or combination of Indicator Features.

9. The method of claim 7, additionally comprising steps to construct a multiclass classifier, wherein the additional steps are:
   i) grouping the Indicator Features and combinations of Indicator Features based on the predicted probabilities and confidence intervals determined by the classifier; and
   ii) forming a new multiclass classifier by assigning a risk level to each grouping of Indicator Features, based on the desired output scale of the classifier.

10. A program storage device readable by a computer tangibly embodying a program of instructions executable by the computer to perform the method steps for generating Indicator Features in high resolution micro-ultrasound prostate images, the method comprising the steps of:
   i) generating a list of Possible Features in the images by:
      a. obtaining a high resolution micro-ultrasound image of prostate tissue and surrounding tissue that contains biopsied prostate tissue, the biopsied prostate tissue having also been biopsied and graded for a stage of cancer, ranging from benign to the highest grade;
      b. segmenting a region of the image corresponding to the biopsied prostate tissue on the basis of contrasting areas in the image, wherein each area constitutes a detectable feature; and
      c. characterizing and providing a unique label to all detectable features and/or combinations of detectable features only in the region of the image that corresponds to biopsied prostate tissue, the detectable features and/or combinations of detectable features with the unique labels comprising the list of Possible Features;
   ii) repeating steps a. through c. until all detectable recurring patterns have been included in the list of Possible Features;
   iii) generating a Table of Candidate Features by:
      d. reading the micro-ultrasound images in an area corresponding to graded prostate tissue which has been graded for a stage of cancer but for which a result for the stage of cancers is not known to a reader so as to identify Candidate Features and/or combinations of Candidate Features, wherein the Candidate Features and/or combinations of Candidate Features are a subset of the list of Possible Features;
      e. recording in the Table of Candidate Features the Candidate Features and/or combinations of Candidate Features observed in the area corresponding to graded prostate tissue;
   iv) eliminating non-predictive features from the Table of Candidate Features by:
      f) performing at least one of:
         1) correlating in the Table of Candidate Features the stage of cancer in the biopsied prostate tissue that corresponds to the area in the image where each of the Candidate Features and/or combinations of Candidate Features are identified, wherein the stage ranges from benign to the highest grade, wherein the correlation is a predicted probability of cancer for a given Candidate Feature or combination of Candidate Features; and
         2) using the Table of Candidate Features as a training set of features to train a linear or nonlinear feature elimination classifier to classify a Candidate Feature or combination of Candidate Features as cancerous or non-cancerous and thereby determining a predicted probability of cancer for a given Candidate Feature or combination of Candidate Features; and
      g. eliminating, from the Table of Candidate Features for generating the Indicator Features, Candidate Features or combinations of Candidate Features that have a predicted probability of cancer that is below a threshold value, the predicted probability of cancer being determined in step f).

11. The program storage device of claim 10, wherein the image is any one or a combination of: B-mode (grey-scale), Velocity Color Flow Imaging, Power Doppler Color Flow Imaging, Elastography, Contrast Enhancement, or Spectral Analysis.

* * * * *